US007771431B2

(12) United States Patent
Scribner et al.

(10) Patent No.: US 7,771,431 B2
(45) Date of Patent: *Aug. 10, 2010

(54) SYSTEMS AND METHODS FOR PLACING MATERIALS INTO BONE

(75) Inventors: Robert M Scribner, Los Altos, CA (US); Michael L Reo, Redwood, CA (US); Mark A Reiley, Piedmont, CA (US); Ryan Boucher, San Francisco, CA (US)

(73) Assignee: Kyphon SÀRL, Neuchâtel (CH)

( * ) Notice: Subject to any disclaimer, the term of this patent is extended or adjusted under 35 U.S.C. 154(b) by 319 days.

This patent is subject to a terminal disclaimer.

(21) Appl. No.: 11/593,284

(22) Filed: Nov. 6, 2006

(65) Prior Publication Data
US 2007/0055283 A1 Mar. 8, 2007

Related U.S. Application Data

(62) Division of application No. 10/617,976, filed on Jul. 11, 2003, now Pat. No. 7,153,307, which is a division of application No. 09/804,107, filed on Mar. 12, 2001, now Pat. No. 6,613,054, which is a division of application No. 09/134,323, filed on Aug. 14, 1998, now Pat. No. 6,241,734.

(51) Int. Cl.
*A61B 17/58* (2006.01)
(52) U.S. Cl. .......................................... 606/93; 606/94
(58) Field of Classification Search .................. 606/92, 606/93, 94, 95
See application file for complete search history.

(56) References Cited

U.S. PATENT DOCUMENTS

| 3,606,086 | A | 9/1971 | Drummond et al. |
| 4,005,527 | A | 2/1977 | Wilson et al. |
| 4,083,369 | A | 4/1978 | Sinnreich |
| 4,086,914 | A | 5/1978 | Moore |
| 4,232,670 | A | 11/1980 | Richter et al. |
| 4,277,184 | A | 7/1981 | Solomon |
| 4,313,434 | A | 2/1982 | Segal |
| 4,323,071 | A | 4/1982 | Simpson et al. |
| 4,327,736 | A | 5/1982 | Inoue |
| 4,338,925 | A | 7/1982 | Miller |

(Continued)

FOREIGN PATENT DOCUMENTS

DE  88 00197  6/1988

(Continued)

OTHER PUBLICATIONS

Smith + Nephew, "Acufex MosaicPlasty—A Lasting solution in the repair of cartilaginous defects," catalog, 1997, Smith + Nephew, Andover, Massachusetts, USA.

(Continued)

*Primary Examiner*—Pedro Philogene
(74) *Attorney, Agent, or Firm*—Haynes and Boone, LLP

(57) ABSTRACT

A method for delivering material into bone deploys a cannula through soft tissue to establish a subcutaneous path into bone. The method deploys a cavity forming instrument through the cannula to form a cavity in cancellous bone. The method introduces a material into the cavity through the cannula, which includes the advancement of a tamping instrument through the cannula to urge material into the cavity.

14 Claims, 19 Drawing Sheets

U.S. PATENT DOCUMENTS

| | | | |
|---|---|---|---|
| 4,576,152 A | 3/1986 | Muller et al. | |
| D283,840 S | 5/1986 | Matsutani | |
| 4,642,094 A | 2/1987 | North, Jr. et al. | |
| 4,643,712 A | 2/1987 | Kulik et al. | |
| 4,653,487 A | 3/1987 | Maale | |
| 4,919,153 A | 4/1990 | Chin | |
| 4,969,888 A * | 11/1990 | Scholten et al. | 606/94 |
| 5,013,318 A | 5/1991 | Spranza, III | |
| 5,108,404 A | 4/1992 | Scholten et al. | |
| 5,116,305 A | 5/1992 | MIlder et al. | |
| 5,171,248 A | 12/1992 | Ellis | |
| 5,254,091 A | 10/1993 | Aliahmad | |
| 5,310,407 A | 5/1994 | Casale | |
| 5,312,333 A * | 5/1994 | Churinetz et al. | 604/57 |
| 5,385,566 A | 1/1995 | Ullmark | |
| 5,415,631 A | 5/1995 | Churinetz et al. | |
| 5,419,765 A | 5/1995 | Weldon et al. | |
| 5,439,447 A | 8/1995 | Miraki | |
| 5,468,245 A | 11/1995 | Vargas, III | |
| 5,470,336 A | 11/1995 | Ling et al. | |
| 5,484,442 A | 1/1996 | Melker et al. | |
| 5,512,054 A * | 4/1996 | Morningstar | 604/191 |
| 5,514,137 A | 5/1996 | Coutts | |
| 5,571,189 A * | 11/1996 | Kuslich | 623/17.12 |
| 5,601,559 A | 2/1997 | Melker et al. | |
| 5,658,310 A | 8/1997 | Berger | |
| 5,718,707 A | 2/1998 | Mikhail | |
| 5,735,831 A | 4/1998 | Johnson et al. | |
| 5,741,261 A | 4/1998 | Moskovitz et al. | |
| 5,788,703 A | 8/1998 | Mittelmeier et al. | |
| 5,800,407 A | 9/1998 | Eldor | |
| 5,824,087 A | 10/1998 | Aspden et al. | |
| 5,827,236 A | 10/1998 | Takahashi | |
| 5,827,289 A | 10/1998 | Reiley et al. | |
| 5,876,383 A | 3/1999 | Grooters et al. | |
| 5,888,220 A * | 3/1999 | Felt et al. | 128/898 |
| 5,919,196 A | 7/1999 | Robic et al. | |
| 5,972,015 A | 10/1999 | Scribner et al. | |
| 5,989,260 A | 11/1999 | Yao | |
| 5,997,581 A | 12/1999 | Khalili | |
| 6,017,348 A | 1/2000 | Hart et al. | |
| 6,042,576 A | 3/2000 | DeVries | |
| 6,048,346 A | 4/2000 | Reiley et al. | |
| 6,083,229 A | 7/2000 | Constantz et al. | |
| 6,146,358 A | 11/2000 | Rowe | |
| 6,146,385 A | 11/2000 | Torrie et al. | |
| 6,149,655 A | 11/2000 | Constantz et al. | |
| 6,235,043 B1 | 5/2001 | Reiley et al. | |
| 6,241,734 B1 * | 6/2001 | Scribner et al. | 606/93 |
| 6,248,110 B1 | 6/2001 | Reiley et al. | |
| 6,348,055 B1 | 2/2002 | Preissman | |
| 6,383,190 B1 * | 5/2002 | Preissman | 606/94 |
| 6,387,087 B1 | 5/2002 | Grooters | |
| 6,395,007 B1 | 5/2002 | Bhatnagar et al. | |
| 6,423,083 B2 | 7/2002 | Reiley et al. | |
| 6,607,544 B1 | 8/2003 | Boucher et al. | |
| 6,613,054 B2 * | 9/2003 | Scribner et al. | 606/93 |
| 6,852,095 B1 | 2/2005 | Ray | |
| 7,153,307 B2 * | 12/2006 | Scribner et al. | 606/93 |

FOREIGN PATENT DOCUMENTS

| | | |
|---|---|---|
| EP | 0 888 752 A2 | 1/1999 |
| EP | 0 890 341 | 1/1999 |
| FR | 2 742 652 | 6/1997 |
| JP | 8038618 | 2/1996 |
| WO | WO 90/04364 | 5/1990 |
| WO | WO 96/39970 | 12/1996 |
| WO | WO 97/26847 | 7/1997 |
| WO | 9856301 | 12/1998 |
| WO | WO 98/56301 | 12/1998 |
| WO | WO 99/08616 | 2/1999 |
| WO | WO 99/49819 | 10/1999 |
| WO | WO 99/51149 | 10/1999 |
| WO | WO 99/62416 | 12/1999 |
| WO | WO 00/54705 | 9/2000 |
| WO | WO 00/67650 | 11/2000 |
| WO | WO 01/28439 | 4/2001 |

OTHER PUBLICATIONS

Gangi, Afshin, "Percutaneous Vertebroplasty Guided by a Combination of CT and Fluoroscopy," Article, Jan. 1994, Ameridcan Society of Neuroradiology, USA.

Deramond, H., "Percutaneous Vertebroplasty," Article, Jun. 1997, Seminars in Musculoskeletal Radiology, vol. 1, No. 2, New York, USA.

Galibert, P., et al., "Note Preliminaire Sur Le Traitement Des Angiomes Vertebraux Par Vertebroplastie Acrylique Percutanee," Neurochinurgie, 33:166-168 (Apr. 1987) France.

\* cited by examiner

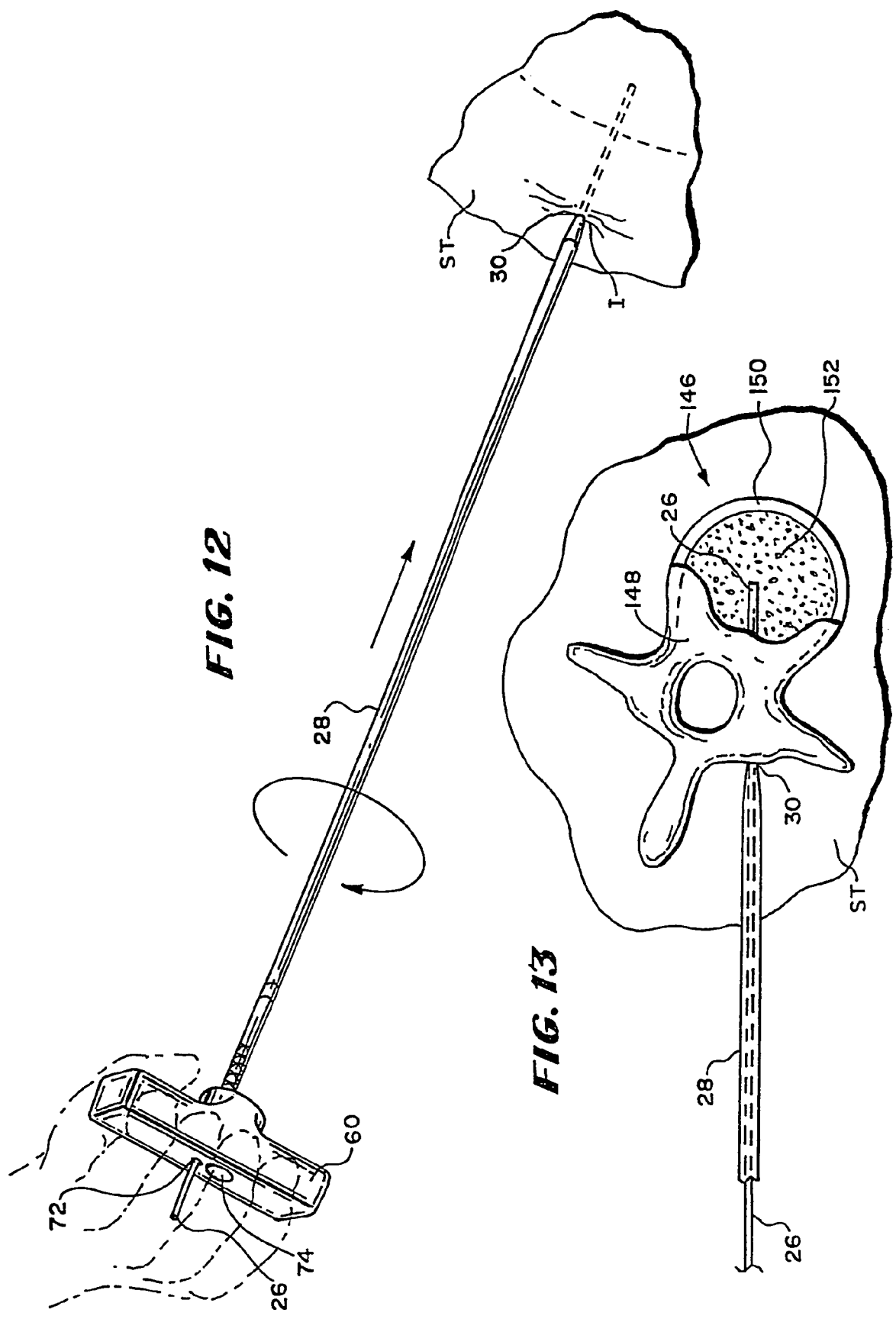

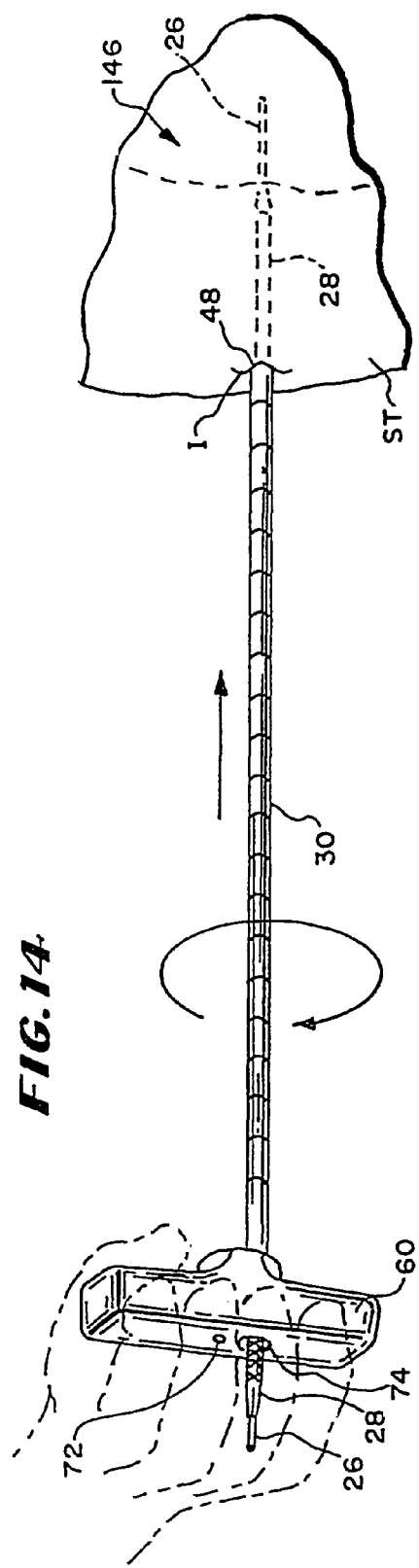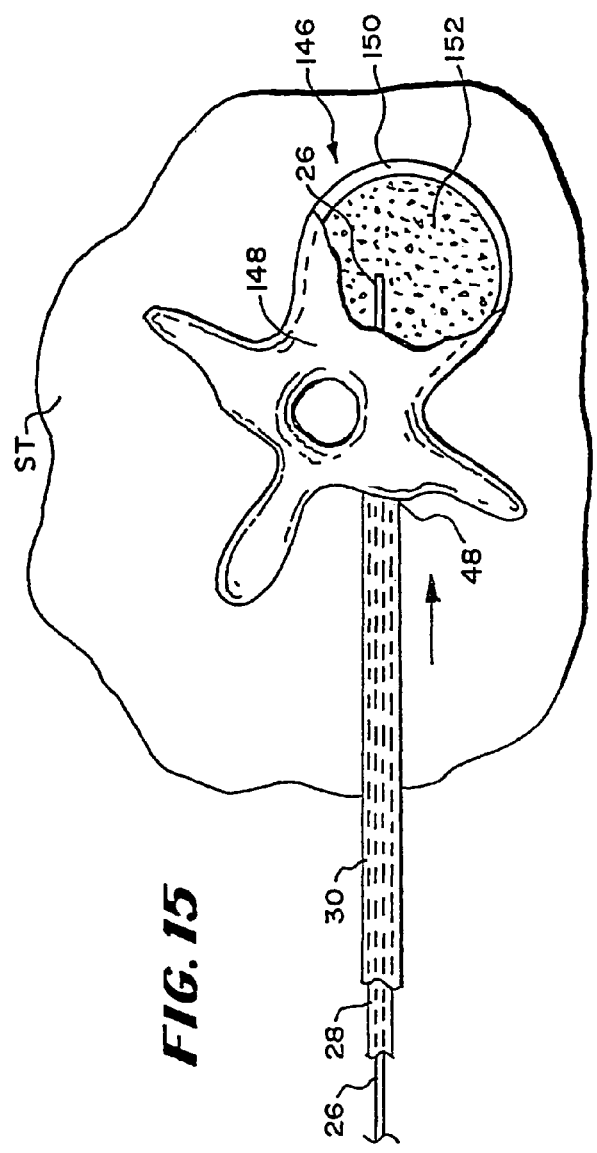
FIG. 14
FIG. 15

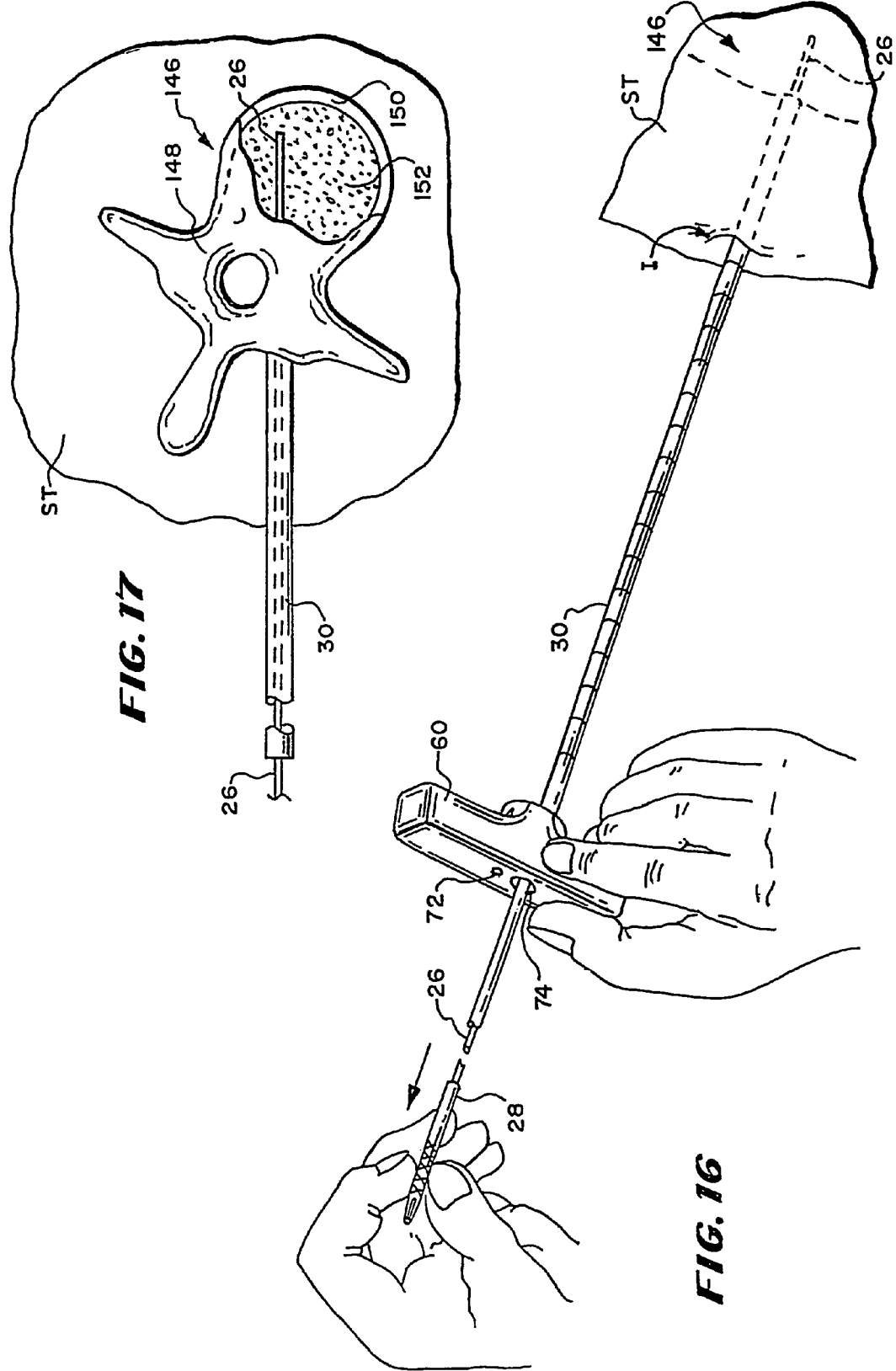

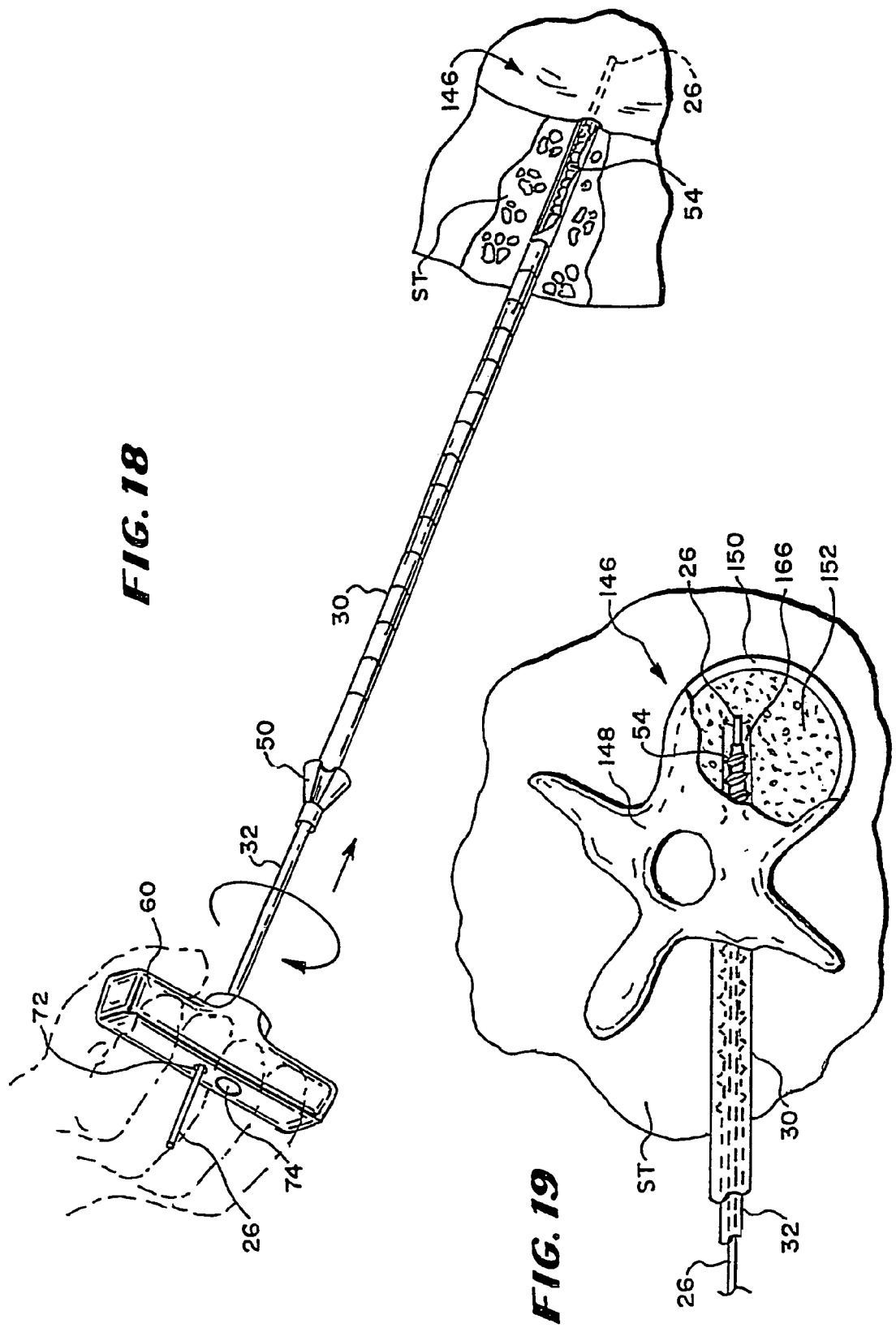

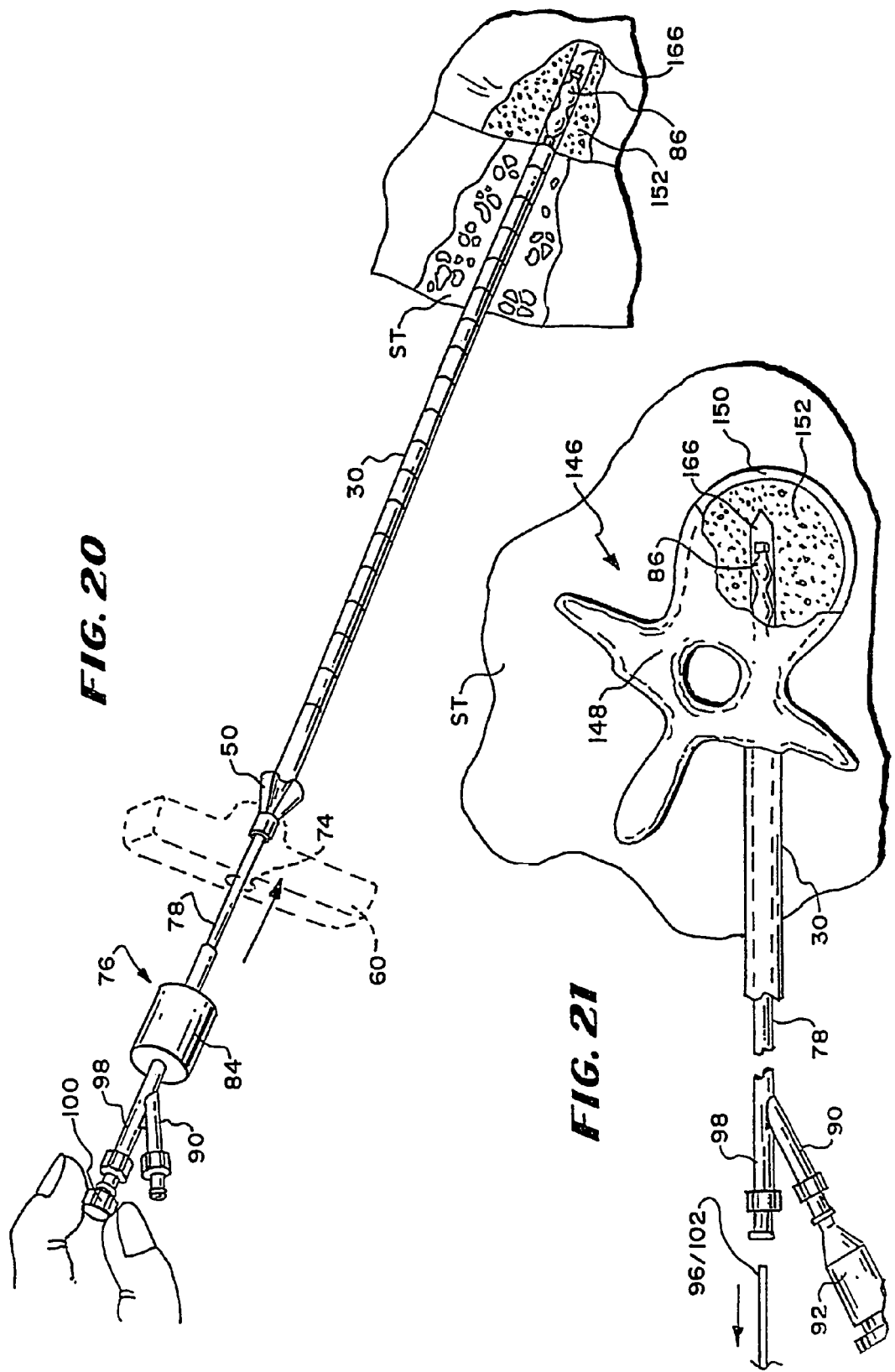

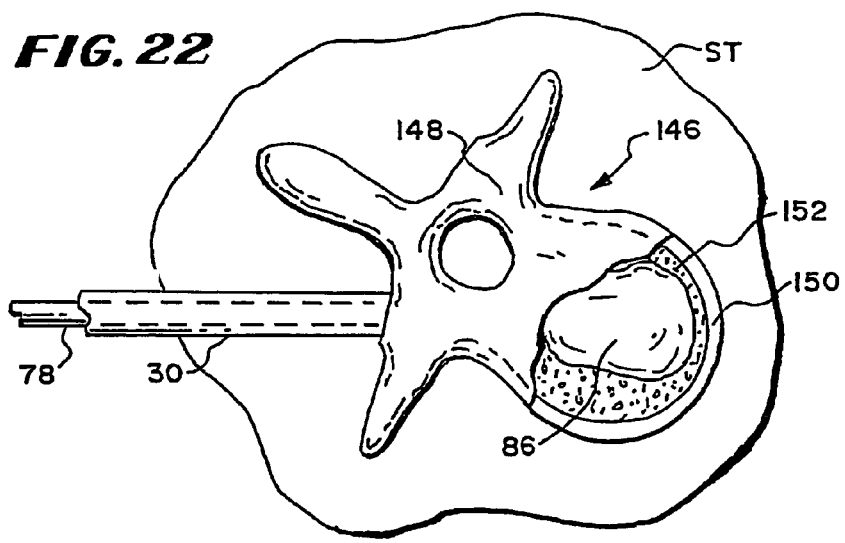
FIG. 22
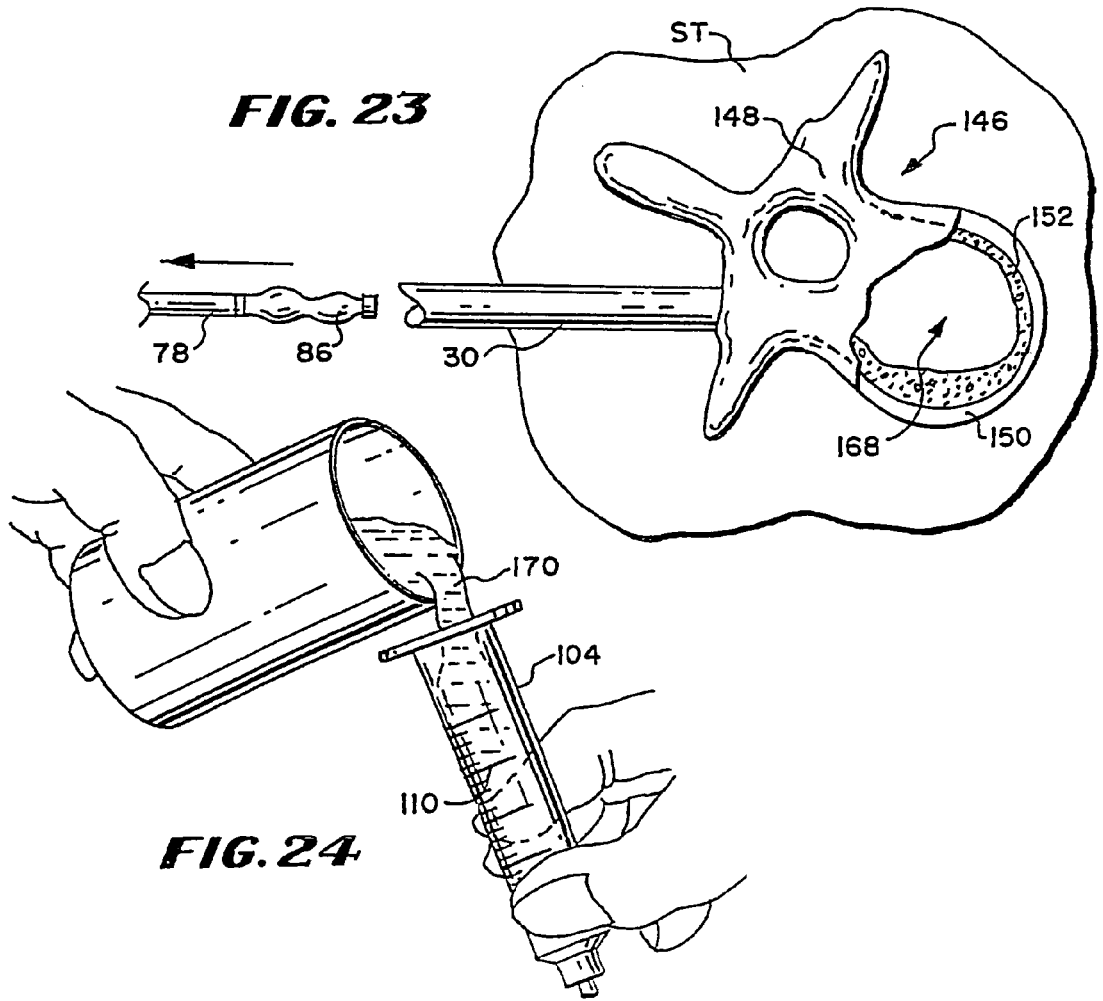
FIG. 23
FIG. 24

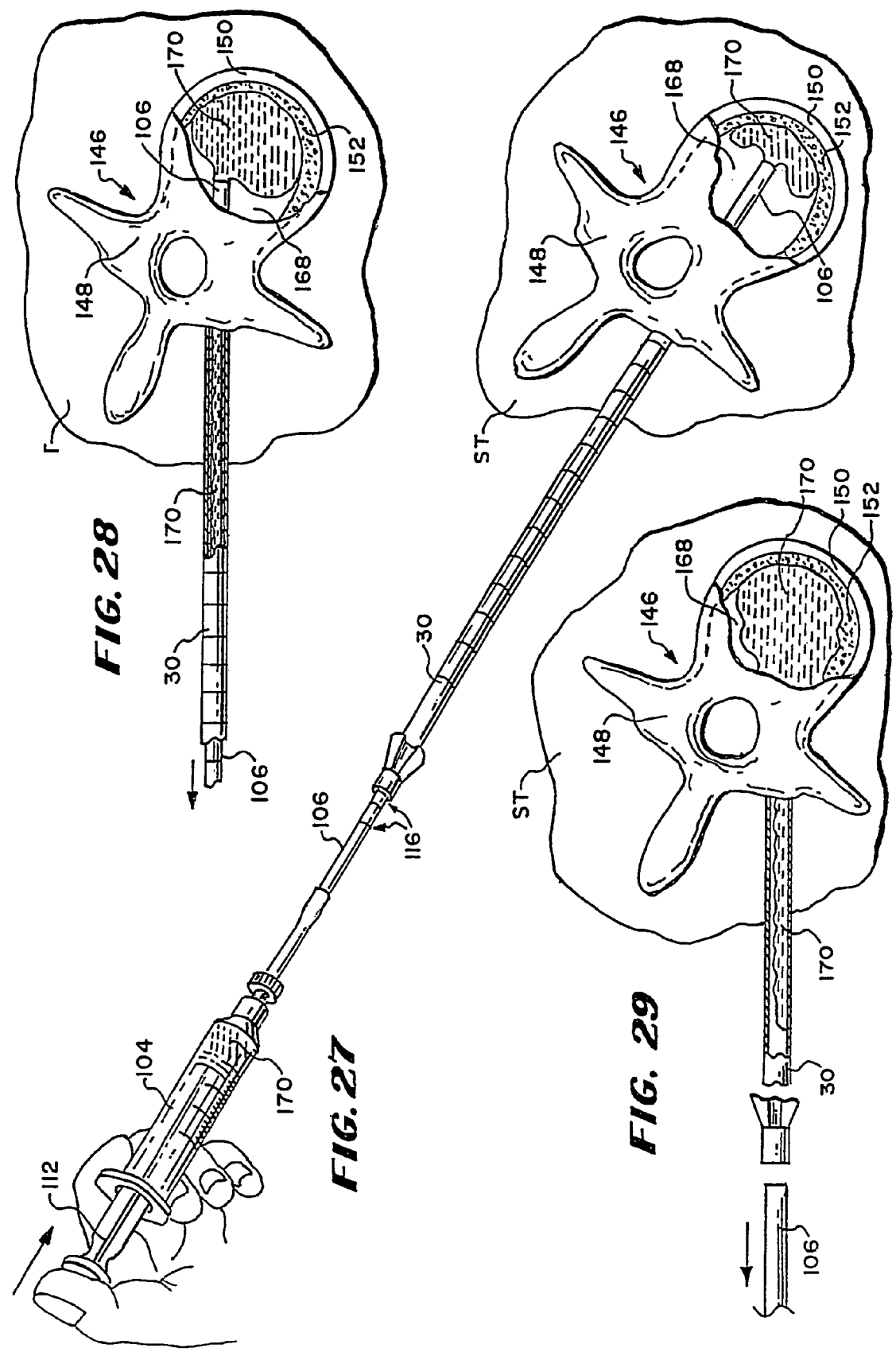

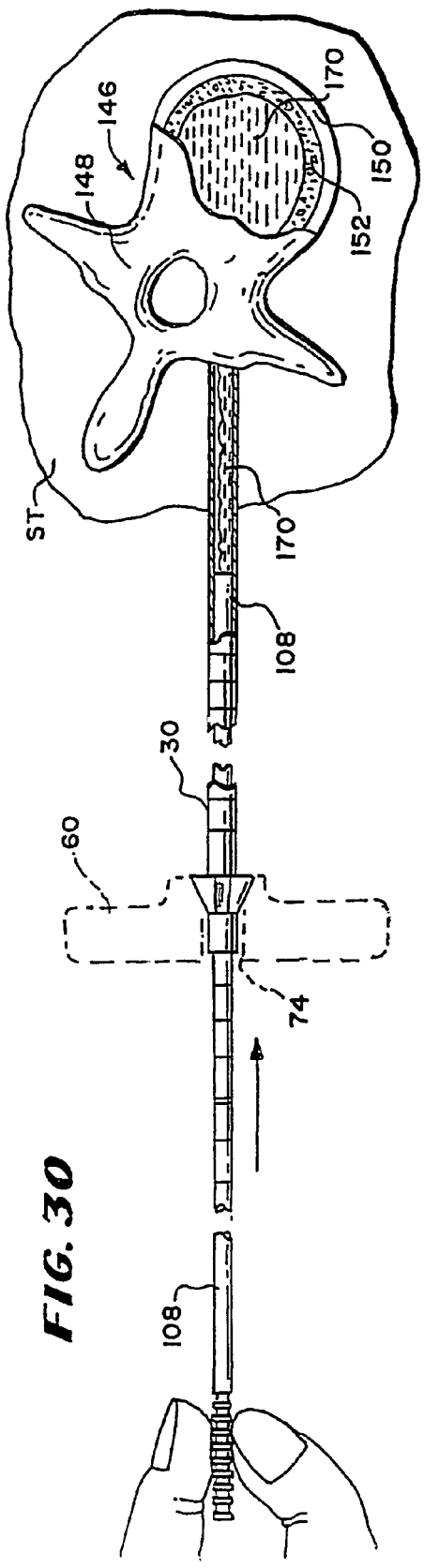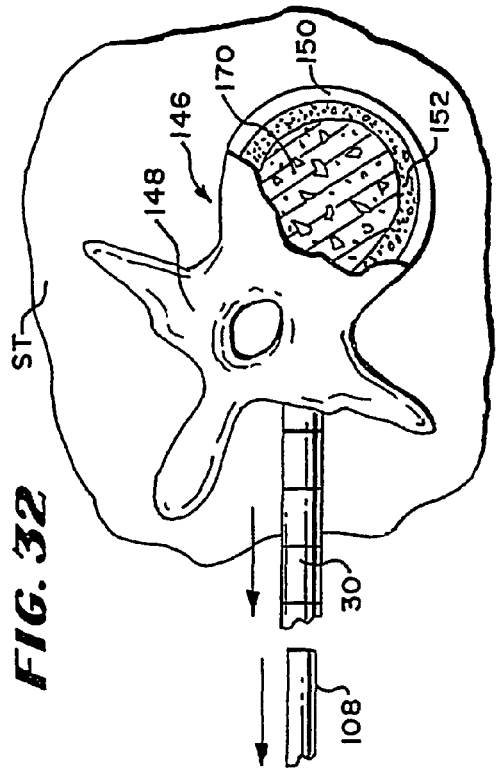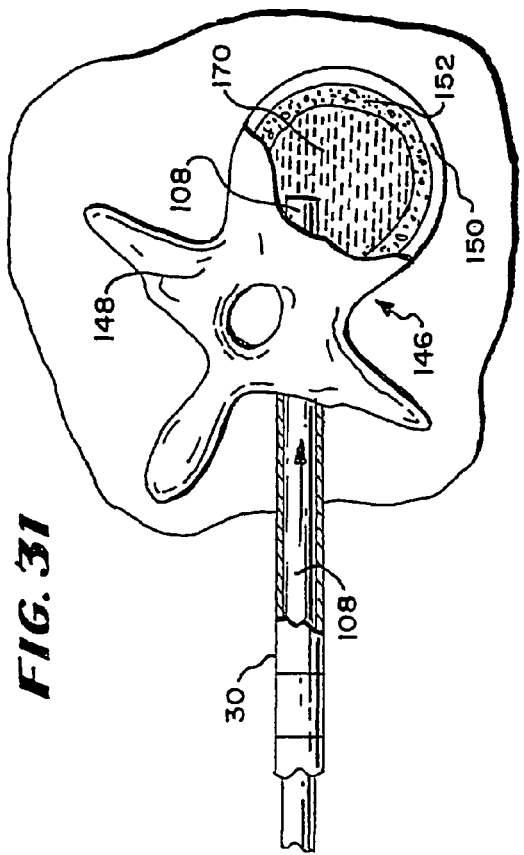
FIG. 30
FIG. 32
FIG. 31

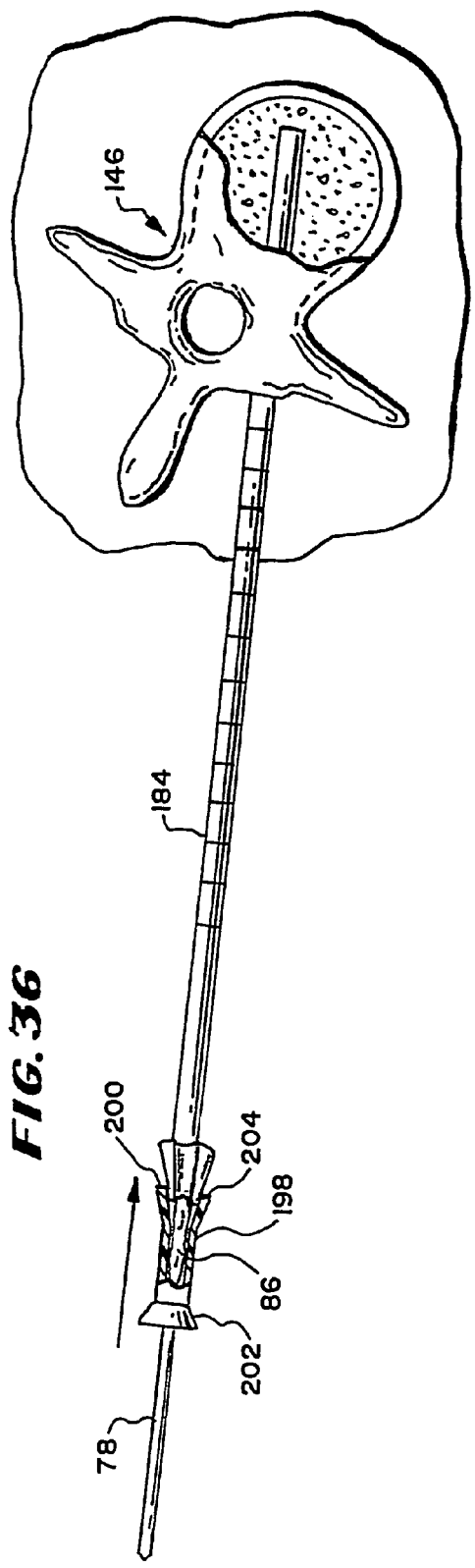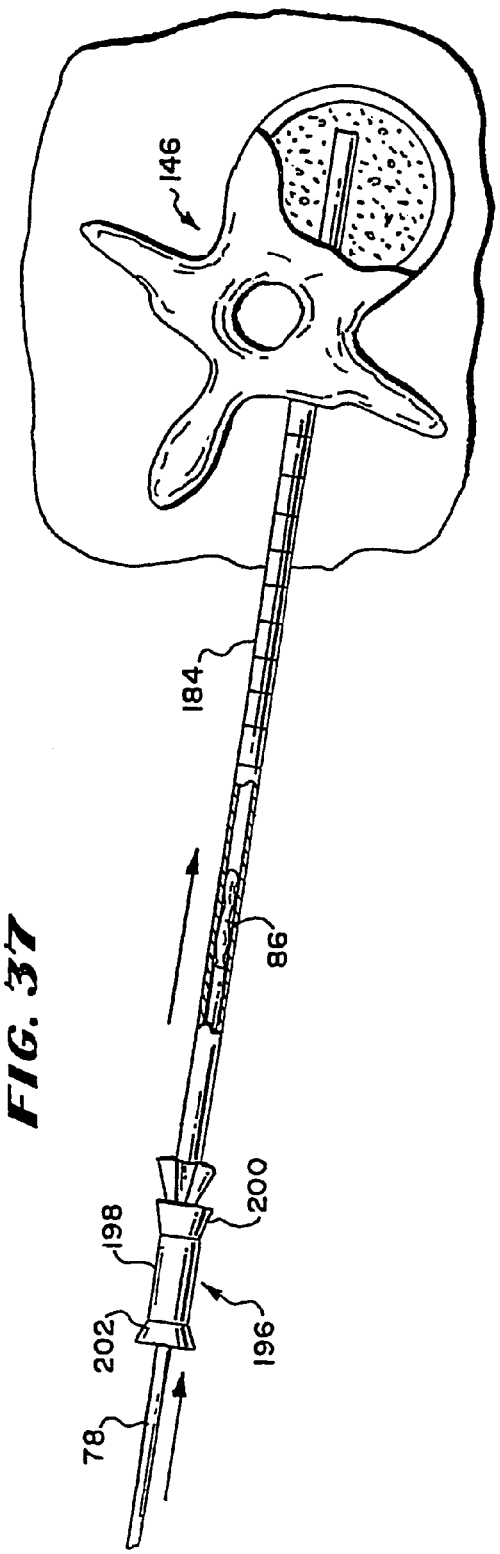

SYSTEMS AND METHODS FOR PLACING MATERIALS INTO BONE

RELATED APPLICATIONS

This application is a divisional of U.S. patent application Ser. No. 10/617,976, filed Jul. 11, 2003, now U.S. Pat. No. 7,153,307, and entitled "Systems and Methods for Placing Materials into Bone," which is a divisional of U.S. patent application Ser. No. 09/804,107, filed Mar. 12, 2001, now U.S. Pat. No. 6,613,054, which is a divisional of application Ser. No. 09/134,323, filed Aug. 14, 1998, now U.S. Pat. No. 6,241,734.

FIELD OF THE INVENTION

The invention generally relates to the treatment of bone conditions in humans and other animals.

BACKGROUND OF THE INVENTION

Injection devices similar to a household caulking gun are used to inject bone cement into bone. A typical bone cement injection device has a pistol shaped body, which supports a cartridge containing bone cement. A trigger actuates a spring-loaded ram, which forces a volume of bone cement in a viscous condition through a suitable nozzle and into the interior of a bone targeted for treatment. According to the teachings of U.S. Pat. Nos. 4,969,888 and 5,108,404, a cavity can be first formed by compacting cancellous bone inside the bone, into which the bone cement is injected. Conventional cement injection devices provide no opportunity to override the spring action and quickly terminate the flow of cement, should the cavity fill before the spring-actuated load cycle is completed. Furthermore, once the spring-actuated mechanism is triggered, conventional cement injection devices do not permit the injection volume or inject rate to be adjusted or controlled in real time, in reaction to cancellous bone volume and density conditions encountered inside bone.

In a clinical procedure called vertebroplasty, bone cement is injected at high pressure (typically, about 700 psi) into the interior of a vertebral body, without the prior formation of a cavity. Because high pressure is used, there is little opportunity to quickly and accurately adjust cement flow in reaction to bone volume and density conditions encountered. Momentum generated by high pressure-induced cement flow continues to propel cement into the targeted bone site even after termination of the high pressure.

As a result of the relatively high pressure that conventional procedures rely upon, coupled with the effective lack of a short response time, the targeted bone interior can suddenly overfill. Excess filling material can be forced outside the bone interior, and into adjoining tissue regions, where the presence of filling material is not required or desired.

For these and other reasons, there is a need for new systems and methods for placing material into bones, with greater rate and volume control, a faster response time, and without requiring the use of high pressure.

SUMMARY OF THE INVENTION

The invention provides instruments, systems, and methods, which, in use, enable greater control over the placement of materials into bone.

One aspect of the invention provides A method that deploys a cannula through soft tissue to establish a subcutaneous path into bone. The method deploys a cavity forming instrument through the cannula to form a cavity in cancellous bone. The method introduces a material into the cavity through the cannula, including advancing a tamping instrument through the cannula to urge material into the cavity. The tamping instrument urges the material into the cavity at a low delivery pressure. As used herein, a Alow delivery pressure@ is equivalent to the pressure at which liquid is expressed from 1 cc syringe by the application of moderate force to the syringe piston, which amounts to a pressure that is no greater than about 360 psi.

The material can comprise medication or a material that sets to a hardened condition e.g., bone cement, or autograft tissue, or allograft tissue, or synthetic bone substitute, or combinations thereof.

Features and advantages of the inventions are set forth in the following Description and Drawings, as well as in the appended Claims.

BRIEF DESCRIPTION OF THE DRAWINGS

FIG. 12 is a perspective view showing a subsequent step, after insertion of the guide pin instrument shown in FIGS. 9 to 11, which deploys an obturator instrument deployed over the guide pin instrument with aid of a handle;

FIG. 13 is a top view of the vertebral body, with the obturator instrument shown in FIG. 12 deployed;

FIG. 14 is a perspective view showing a subsequent step, after insertion of the obturator instrument shown in FIG. 12, which uses the handle shown in FIG. 12 to aid in the deployment of a cannula instrument over the obturator instrument;

FIG. 15 is a top view of the vertebral body, with the cannula instrument shown in FIG. 14 deployed;

FIG. 16 is a perspective view showing a subsequent step, after insertion of the cannula instrument shown in FIG. 14, which removes the obturator instrument from the cannula instrument, to leave the cannula instrument and guide pin instrument in place;

FIG. 17 is a top view of the vertebral body, after the obturator removal step shown in FIG. 16, leaving the cannula instrument and guide pin instrument in place;

FIG. 18 is a perspective view showing a subsequent step, after removal of the obturator instrument shown in FIG. 16, which uses the handle shown in FIG. 14 to aid in the deployment of a drill bit instrument through the cannula instrument along the guide pin instrument;

FIG. 19 is a top view of the vertebral body, as the drill bit instrument shown in FIG. 18 is deployed with aid of the handle to open a passage into the interior volume of the vertebral body;

FIG. 20 is a perspective view showing a subsequent step, after removal of the drill bit instrument and guide pin instrument shown in FIG. 18, of deploying the cavity forming instrument into the vertebral body;

FIG. 21 is a top view of the vertebral body, as the expandable structure carried by the cavity forming instrument shown in FIG. 20 is deployed into the interior volume of the vertebral body;

FIG. 22 is a top view of the vertebral body, as the expandable structure shown in a collapsed condition in FIG. 21 is expanded to compact cancellous bone and form a cavity;

FIG. 23 is a top view of the vertebral body, after removal of the expandable structure, showing the cavity formed by compacting cancellous bone;

FIG. 24 is a perspective view of the syringe of the material introducing instrument group, shown in FIG. 5, being filled with a material selected for introduction into the cavity shown in FIG. 23;

FIGS. 27 and 28 are perspective and top views, respectively, showing the syringe and attached nozzle shown in FIG. 26 in use to inject material into the cannula instrument for passage into the cavity;

FIG. 29 is a top view of the vertebral body after a measured volume of material has been injected and the syringe and attached nozzle withdrawn from the cannula instrument;

FIG. 30 is a top view showing the deployment of a tamping instrument, which forms a part of the material introducing instrument group shown in FIG. 5, being deployed in the cannula instrument;

FIG. 31 is a top view showing advancement of the tamping instrument in the cannula instrument to displace and distribute material from the cannula instrument into the cavity;

FIG. 32 is a top view of the vertebral body after removal of the tamping instrument and cannula instrument, showing the cavity, now filled with the material;

FIG. 36 is a perspective view of the cavity forming structure shown in FIG. 35, with the introducer sleeve (shown partially in section) coupled to the proximal end of the cannula instrument, to guide the expandable structure compressed within the sleeve into the reduced diameter cannula instrument without damage; and, FIG. 37 is a perspective view of the cavity forming structure shown in FIG. 36, after the expandable structure has been guided by the introducer sleeve into the cannula instrument and is being advanced through the cannula instrument for deployment in bone.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENT

Figure 1:
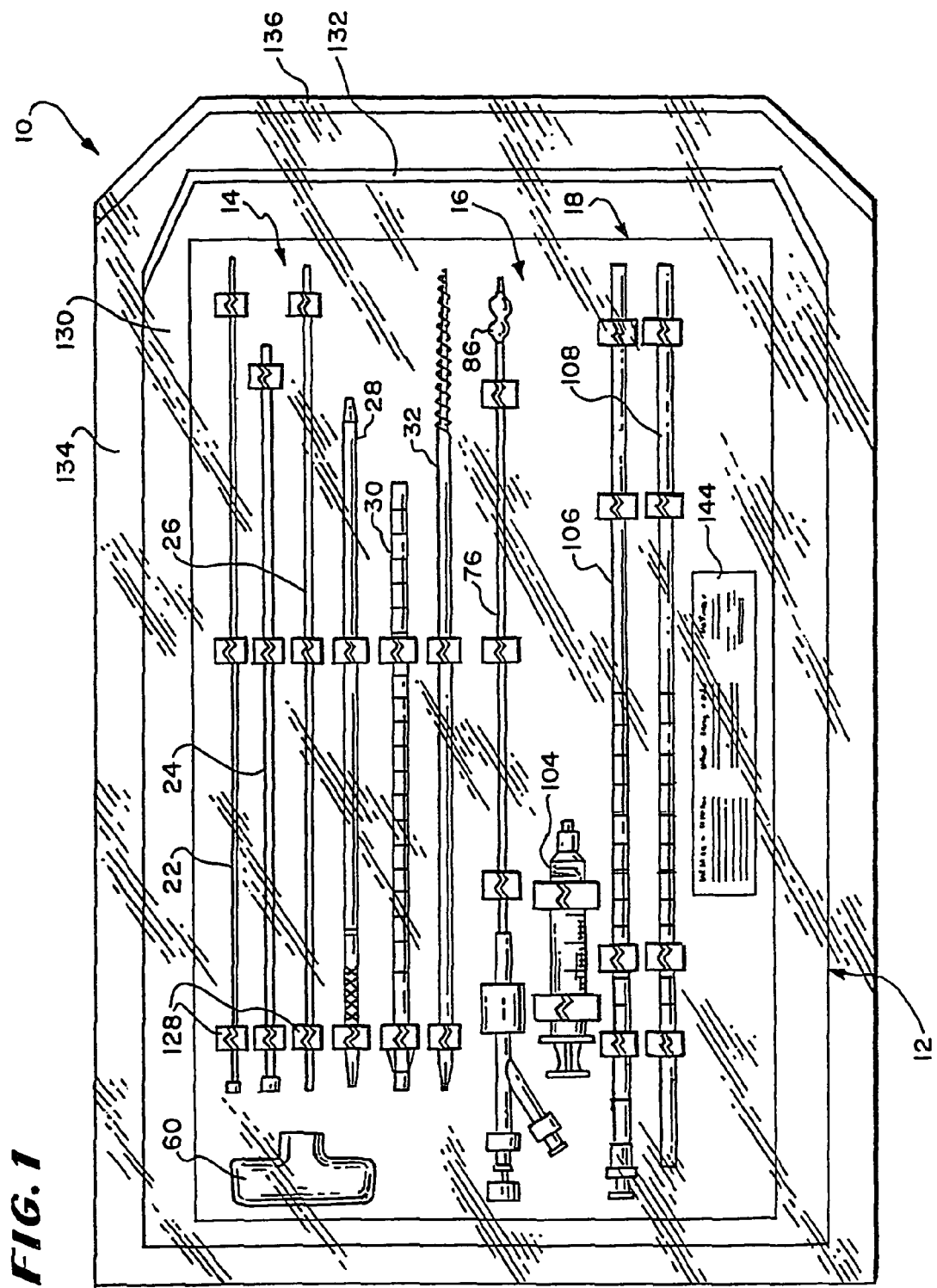
FIG. 1 is a plane view of a kit housing a system of functional instruments, which, in use, gain subcutaneous access to the inside of a bone to compact cancellous bone and form a cavity for therapeutic purposes.
Figure 2:
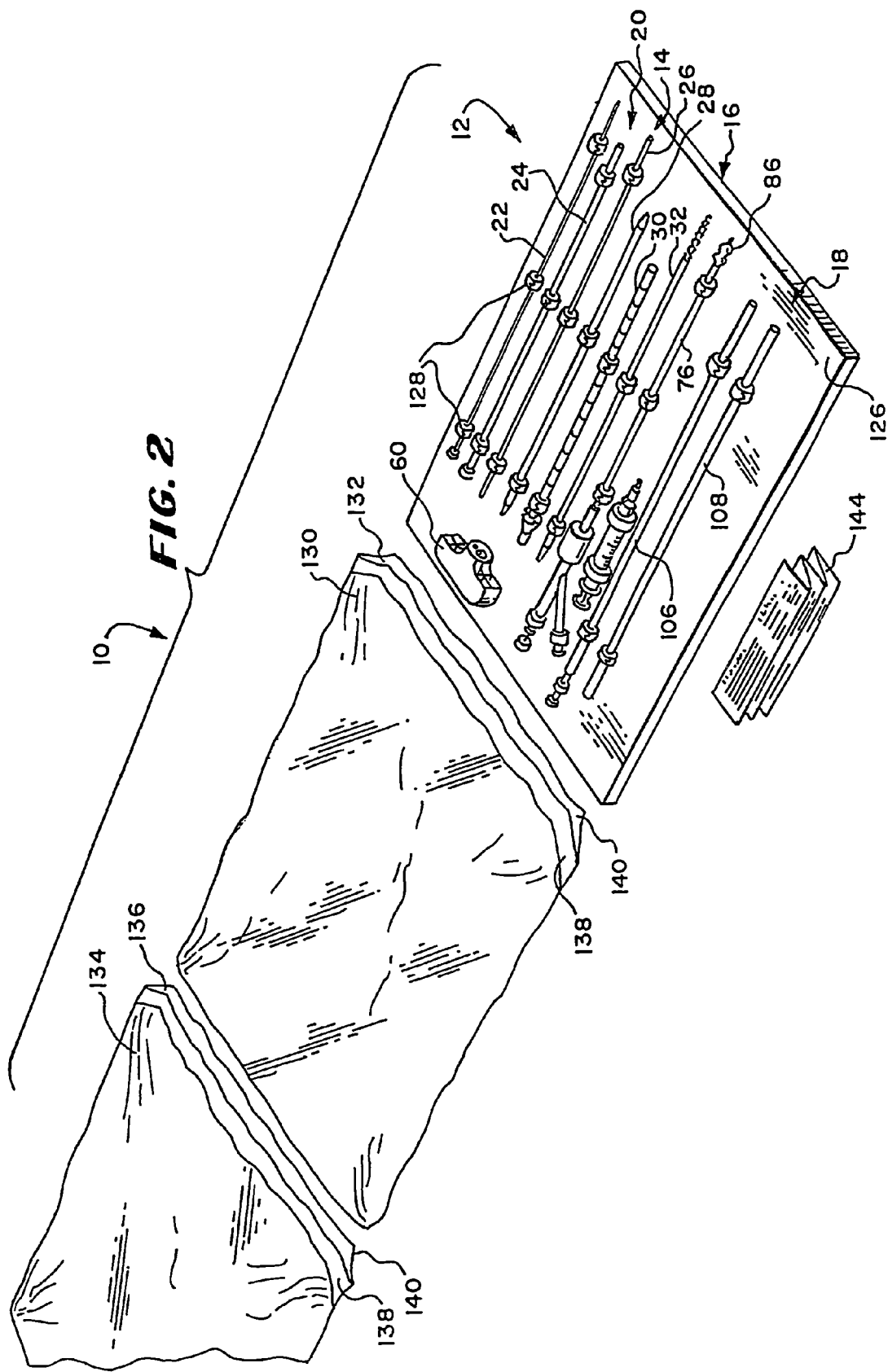
FIG. 2 is an exploded perspective view of the kit shown in FIG. 1.

FIGS. 1 and 2 show a system 10 of functional instruments. In use, certain instruments of the system 10 are deployed in a purposeful manner to penetrate tissue and gain subcutaneous access to the inside of a bone. Inside bone, other instruments of the system 10 are deployed to form a cavity in cancellous bone, into which a material is placed for therapeutic purposes.

Figure 3:
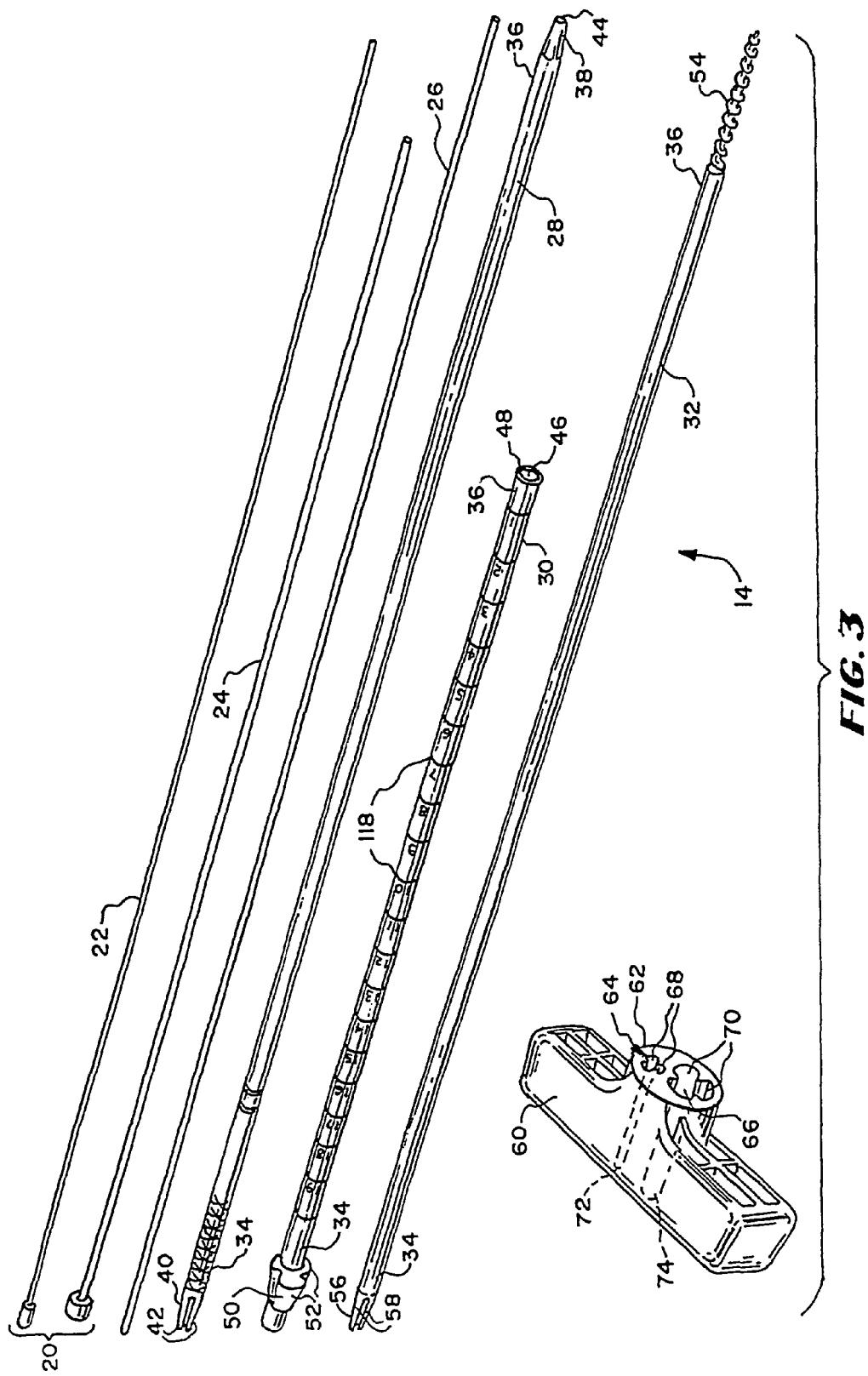
FIG. 3 is a perspective view of the subcutaneous access instrument group that forms a part of the system shown in FIG. 1.
Figure 4:
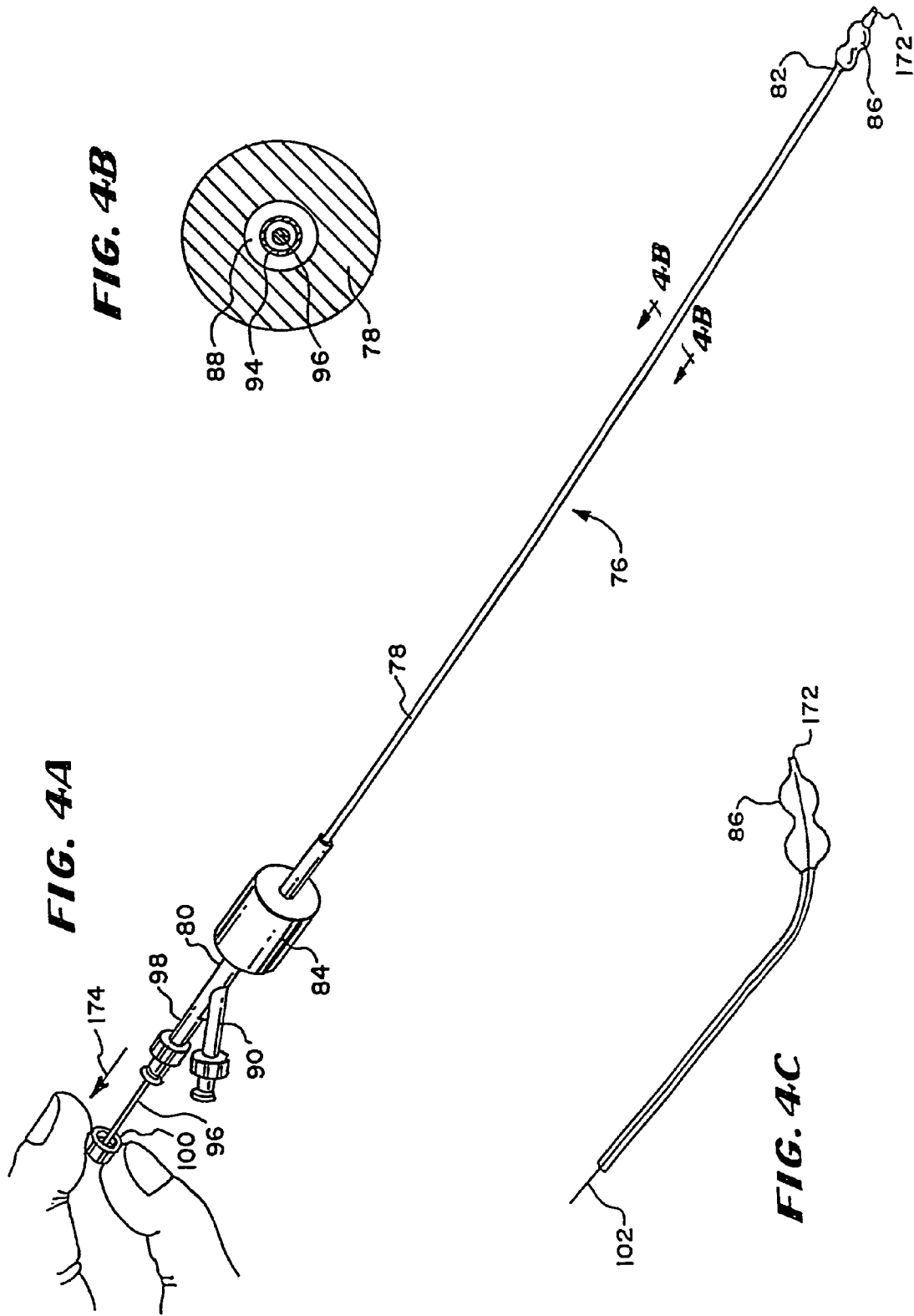
FIG. 4A is a perspective view of the cavity forming instrument that forms a part of the system shown in FIG. 1.
FIG. 4B is a section view of the catheter tube of the cavity forming instrument, taken generally along line 4B-4B in FIG. 1.
FIG. 4C is an end view of an alternative embodiment of the cavity forming instrument shown in FIG. 4A, having a prebent stylet.
Figure 5:
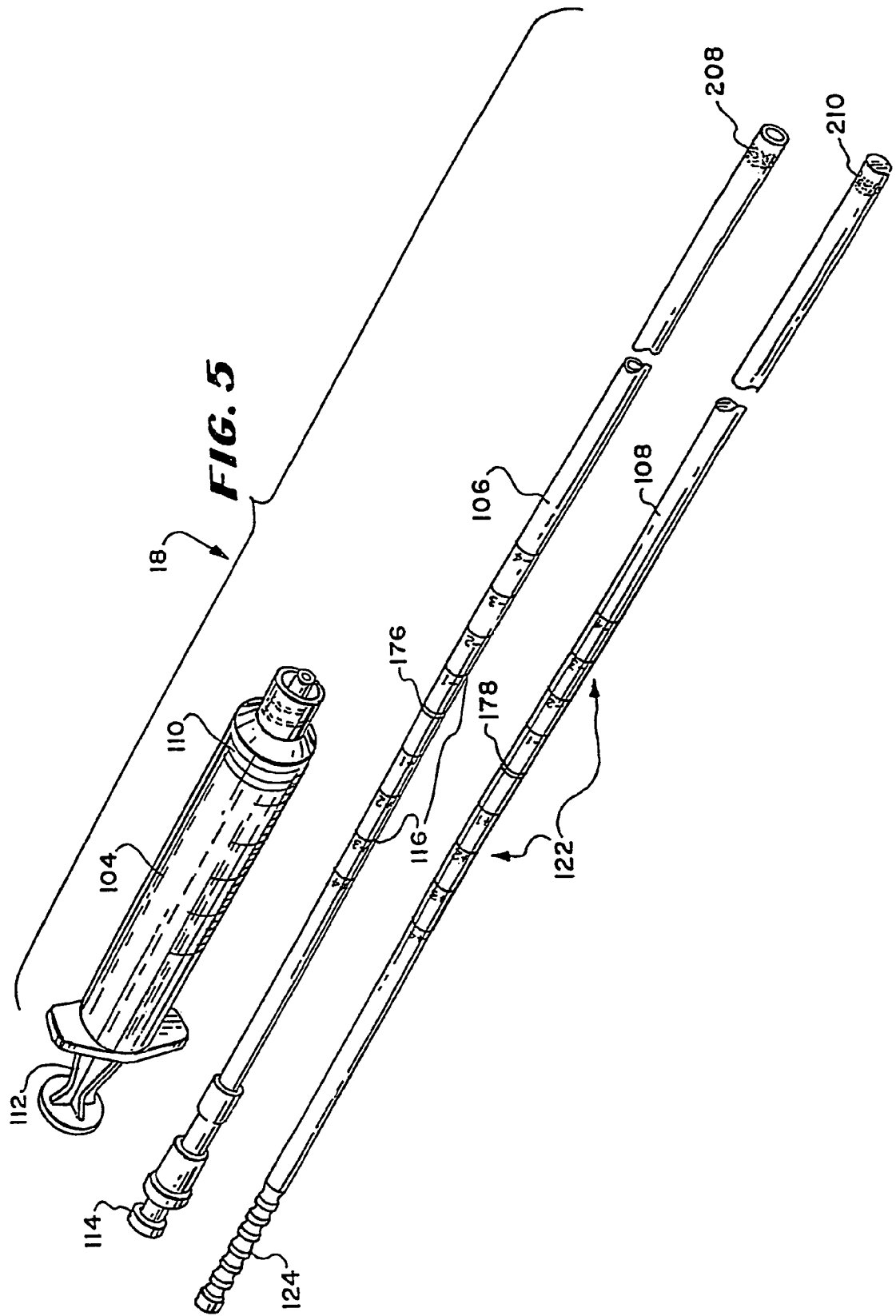
FIG. 5 is a perspective view of the material introducing instrument group that forms a part of the system shown in FIG. 1.

In the illustrated embodiment, the system 10 is arranged as a prepackage kit 12 in three functional instrument groups 14, 16, and 18. The first group 14 (which FIG. 3 shows outside the kit 12) comprises instruments whose purpose is to gain subcutaneous access to a bone interior. The second group 16 (which FIG. 4 shows outside the kit 12) comprises an instrument whose function is to create a cavity in cancellous bone. The third group 18 (which FIG. 5 shows outside the kit 12) comprises instruments whose function is to introduce a material into the cavity.

The kit 12 can take various forms. In the illustrated embodiment, the kit 12 comprises a sterile, wrapped assembly.

Further details of each functional instrument group 14, 16, and 18 and the kit 12 follow.

I. The Subcutaneous Access Instrument Group

The number and type of instruments in the group 14 can vary. FIG. 3 shows five representative instruments, each having a different size and function.

A. The Spinal Needle and Guide Pin

As FIG. 3 shows, one instrument comprises a conventional spinal needle assembly 20 and a guide pin instrument 26.

In use, the spinal needle assembly 20 establishes the initial subcutaneous path leading to the targeted treatment site. The guide pin instrument 26 is deployed through this path, followed by progressively larger instruments, as will be described later.

The spinal needle assembly 20 comprises a stylet 22, which is slidably deployed within a stylus 24. The stylus 24 typically has, for example, about an eleven gauge diameter. Other gauge diameters can be used, according to the gauge of the guide pin instrument 26 used.

In use, the guide pin instrument 26 is deployed through the subcutaneous path established by the spinal needle assembly 20, by exchange with the needle stylet 22. The guide pin instrument 26 serves to guide the establishment of the main operative pathway to the targeted treatment site.

The remaining instruments 28, 30, and 32 in the group 14 share some common features, although they are intended, in use, to perform different functions. These instruments 28, 30, and 32 are each made of a rigid, surgical grade plastic or metal material. These instruments 28, 30, and 32 each comprises an elongated, cylindrical body having a proximal end 34 and a distal end 36.

B. The Obturator Instrument

The instrument 28 functions as an obturator. Its distal end 36 is tapered to present a penetrating surface 38. In use, the surface 38 is intended to penetrate soft tissue in response to pushing or twisting forces applied by the physician at the proximal end 34.

The proximal end 34 of the obturator instrument 28 presents a flanged surface 40, which tapers from a larger outer diameter to a smaller outer diameter in the direction of the proximal end 34. The flanged surface 40 includes an array of circumferentially spaced teeth 42.

An interior lumen 44 extends through the obturator instrument 28 from the distal end 36 to the proximal end 34. The interior lumen 44 is sized to accommodate the guide pin instrument 26, as will be described in greater detail later.

C. The Cannula Instrument

The instrument 30 functions as a cannula or guide sheath. The cannula instrument 30 is somewhat larger in diameter than and not as long as the obturator instrument 28. The cannula instrument 30 includes an interior lumen 46 that extends from its distal end 36 to its proximal end 34. The interior lumen 46 is sized to accept the obturator instrument 28. The size of the interior lumen 46 permits a physician to slide and rotate the cannula instrument 30 relative to the obturator instrument 28, and vice versa, as will be described in greater detail later.

The distal end 36 of the cannula instrument 30 presents an end surface 48. In use, the end surface 48 of the cannula instrument 30 is intended to penetrate soft tissue surrounding the obturator instrument 28 in response to pushing or twisting forces applied at the proximal end 34.

The proximal end 34 carries an enlarged fitting 50. The fitting 50 tapers from a larger diameter to a smaller diameter in the direction of the proximal end 34. Like the tapered flange 40 on the obturator instrument 28, the tapered fitting 50 has an array of circumferentially spaced teeth 52. The tapered fitting 50 of the cannula instrument 30 possesses a larger maximum outer diameter than the maximum outer diameter of the tapered flange 40 of the obturator instrument 28.

The cannula instrument 30 includes measured markings 118 along its length (see FIG. 3). The measured markings 118 gauge the depth of insertion. The markings 118 can be placed, for example, at one centimeter intervals. As FIG. 3 shows, the markings 118 can be consecutively numbered, beginning at the distal end 36, so that the physician can ascertain the insertion depth at a glance.

D. The Drill Bit Instrument

The instrument 32 functions as a drill bit. The drill bit instrument 32 has generally the same physical dimensions as the obturator instrument 28. Like the obturator instrument 28, the drill bit instrument 32 is intended, in use, to fit for sliding and rotational movement within the interior lumen 46 of the cannula instrument 30.

The distal end 36 of the drill bit instrument 32 includes machined cutting edges 54. In use, the cutting edges 54 are intended to penetrate hard tissue in response to rotation and longitudinal load forces applied at the proximal end 34 of the drill bit instrument 32.

The proximal end 34 presents a tapered flange 56, which is substantially identical to the flange 40 on the obturator instrument 28. Like the obturator instrument 28, the tapered flange 56 changes from a larger diameter to a smaller diameter in the direction of the proximal end 34. The tapered flange 56 of the drill bit instrument 32 also includes an array of circumferentially spaced teeth 58. The form and orientation of the teeth 58 on the drill bit instrument 32 correspond to the form and orientation of the teeth 42 on the obturator instrument 28.

E. The Handle

The group includes a handle 60. The handle 60 engages the functional instruments 28, 30, and 32 in a removable, slip fit fashion to aid a physician in manipulating the instruments during use.

The handle 60 is made from a molded or cast rigid plastic or metal material. The handle 60 is shaped to be comfortably and securely grasped by a normal human hand. The shape and size to accommodate this function can, of course, vary. In the illustrated embodiment, the handle 60 is elongated along a main axis to fit comfortably across the palm of the hand.

The handle 60 includes a center post 62, which is integrally molded to the handle 60 about its geometric center. The center post 62 extends downward to give the handle 60 a general T-shape.

The handle 60 includes two interior cavities or sockets 64 and 66 in the center post 62. The sockets guide the attachment between the handle 60 and the instruments 28, 30, and 32. The first and second sockets 64 and 66 are sized to present unique attachment sites for different functional instruments.

The first socket 64 includes an array of circumferentially spaced grooves 68, which, in form and orientation, match the teeth 42 and 58 at the proximal ends 34 of the obturator instrument 28 and the drill bit instrument 32. The first socket 64 accepts the tapered flange 40 or 56 of either the obturator instrument 28 or the drill bit instrument 32. The teeth 42 and 58 of either tapered flange 40 or 56 mesh in a slip-fit with the grooves 68 of the first socket 64. The running slip-fit allows longitudinal force to be applied to either instrument 28 or 32 through the handle 60. The running slip-fit also prevents relative rotation between either instrument 28 or 32 and the first socket 64, thereby permitting torsional or twisting forces to be applied to either instrument 28 or 32 by the handle 60, with an increased mechanical advantage.

The second socket 66 is larger than the first socket 64 and is sized to accept the larger tapered fitting 50 of the cannula instrument 30. The second socket 66 includes an array of circumferentially spaced grooves 70, which, in form and orientation, match the teeth 52 on the tapered fitting 50. The teeth 52 of the tapered fitting 50 mesh in a slip-fit with the grooves 70 of the second socket 66. The running slip-fit allows both longitudinal and torsional forces to be applied to the cannula instrument 30 through the handle 60, with increased mechanical advantage.

As shown in phantom lines in FIG. 3, a first passage 72 extends through the top of the handle 60, through the center post 62, and into the first socket 64. The passage 72 is generally aligned with the center of the first socket 64 and is sized to pass the guide pin instrument 26 (see FIG. 12).

Likewise, as also shown in phantom lines in FIG. 3) a second passage 74 extends through the top of the handle 60, through the center post 62, and into the second socket 66. The passage 74 is generally aligned with the center of the second socket 66 and is sized to pass the either obturator instrument 28 or the drill bit instrument 32 (see FIG. 14).

Further details of the handle 60 can be found in co-pending U.S. patent application Ser. No. 09/014,229, filed Jan. 27, 1998, and entitled AA Slip-Fit Handle for Hand-Held Instruments that Access Interior Body Regions.

Further details regarding the use of the handle 60 and the associated instruments 26, 28, and 30 will be provided later.

II. The Cavity Forming Instrument

As FIG. 4A shows, the group 16 includes an instrument 76, which is deployed through the cannula instrument 30 to a location inside bone (see FIG. 20). When so deployed, the instrument 76 serves to form a cavity in cancellous bone.

The instrument 76 can be constructed in various ways. In the illustrated embodiment, the instrument 76 includes a flexible catheter tube 78 having a proximal end 80 and a distal end 82. The proximal end 80 carries a handle grip 84 to facilitate gripping and maneuvering the catheter tube 78. The materials for the catheter tube 78 are selected to facilitate its advancement through the cannula instrument 30. The catheter tube 78 can be constructed, for example, using standard flexible, medical grade plastic materials, like vinyl, nylon, polyethylenes, ionomer, polyurethane, and polyethylene tetraphthalate (PET). The catheter tube 78 can also include more rigid materials to impart greater stiffness and thereby aid in its manipulation. More rigid materials that can be used for this purpose include stainless steel, nickel-titanium alloys (NitinolJ material), and other metal alloys.

The distal end 82 of the instrument 76 carries an expandable structure 86. In the illustrated embodiment, the expandable structure 86 is made from a polyurethane or an elastomer (e.g., silicone or nylon) material. The structure 86 has been preformed to possess a desired shape by exposure to heat and pressure, e.g., through the use of conventional thermoforming techniques. As FIG. 4B shows, the catheter body 78 includes an interior lumen 88, which communicates with the interior of the structure 86. A fitting 90 on the proximal end 80 of the catheter tube 78 (see FIG. 4B) communicates with the lumen 88. The fitting 90 couples the lumen 88 to a source 92 of fluid, e.g., sterile saline (see FIG. 21), or a radiopaque contrast medium.

The fluid is introduced from the source 92 into the structure 86 under positive pressure, causing the structure 86 to expand. During expansion inside bone, the material selected for the structure 86 preferably resists deformation, so that the expanded shape inside bone essentially corresponds to its expanded shape outside bone, i.e., when in an open air environment. This allows the physician to select in an open air environment a structure 86 having an expanded shape desired to meet the targeted therapeutic result, with the confidence that the expanded shape inside bone will be similar in important respects. In addition to being able to expand its volume while resisting deformation inside bone, the material of the structure 86 preferable withstands abrasion, tearing, and puncture when in contact with cancellous bone.

The shape of the structure 86, when expanded inside bone, is selected by the physician, taking into account the morphology and geometry of the site to be treated. The shape of the cancellous bone to be compressed, and the local structures that could be harmed if bone were moved inappropriately, are generally understood by medical professionals using textbooks of human skeletal anatomy along with their knowledge of the site and its disease or injury. The physician is also able to select the expanded shape inside bone based upon prior analysis of the morphology of the targeted bone using, for example, plain film x-ray, fluroscopic x-ray, or MRI or CT scanning. The expanded shape inside bone is selected to optimize the formation of a cavity that, e.g., when filled with a suitable material, provides support across the region of the bone being treated.

As one general guideline, in cases where the bone disease causing fracture (or the risk of fracture) is the loss of cancellous bone mass (as in osteoporosis), the selection of the expanded shape of the structure 86 inside bone should take into account that from 30% to 90% of the cancellous bone volume should be compacted. Another general guideline is the amount that the targeted fractured bone region has been displaced or depressed. The expansion of the structure 86 within the cancellous bone region inside a bone can elevate or push the fractured cortical wall back to or near its anatomic position occupied before fracture occurred.

In the illustrated embodiment (see FIG. 4A), the structure 86 possesses a preformed hour-glass or peanut shape. This shape is selected in contemplation of deploying the structure 86 in a vertebral body, as will be described in greater detail later.

To facilitate deployment of the structure 86 through the cannula instrument 30, the catheter tube 78 includes a second interior lumen 94. The lumen 94 extends from a second fitting 98 on the proximal end 80 of the catheter tube 78, through the body of the cannula tube 78, and through the interior of the structure 86 to the tip end 172 of the structure 86. The lumen 94 receives a generally stiff stylet 96, which can be made from a molded plastic or stainless steel material. The stylet 96 is inserted through the fitting 98 into the lumen 94, and includes a threaded coupling 100 to secure the stylet 96 against movement. The presence of the stylet 96 serves to keep the structure 86 in the desired distally straightened condition during passage through the cannula instrument 30 into the targeted tissue region. Once the structure 86 is free of the cannula instrument 30 and inside bone, the stylet 96 can be withdrawn (shown by arrow 174 in FIG. 4A). This returns normal flexibility to the catheter tube 78 and facilitates manipulation of the structure 86 inside bone. With the stylet 96 withdrawn, the lumen 94 can also serve as a pathway for introducing rinsing liquid or to aspirate debris from the bone.

In the illustrated embodiment, the stylet 96 is biased toward a generally straight condition. In an alternative embodiment (see FIG. 4C), a stylet 102 can have a preformed memory, to normally bend its distal region. The memory is overcome to straighten the stylet 102 when confined within the cannula instrument 30. However, as the structure 86 and distal region of the preformed stylet 102 advance free of the cannula instrument 30, to pass into the targeted region, the preformed memory bends the distal region of the stylet 102 and thereby shifts the main axis of the expandable structure 86. The prebent stylet 102, positioned within the interior of the structure 86, aids in altering the orientation of the structure 86, bringing it into better anatomic alignment with the targeted region.

Other types of instruments that can form cavities in cancellous bone and other interior body regions are described in copending U.S. patent application Ser. No. 09/055,805, entitled A Structures and Methods for Creating Cavities in Interior Body Regions, filed Apr. 6, 1998.

III. The Material Introducing Instrument Group

The group 18 includes instruments 104, 106, and 108 which serve to convey and compact a selected material inside the cavity formed by the structure 86. The material in the cavity provides a desired therapeutic result, e.g., replacement of tissue mass, or renewed interior support for the bone, or the delivery of medication, or combinations thereof. Accordingly, the material to perform this function can be selected from among, e.g., a material that sets to a hardened condition, including bone cement, autograft tissue, allograft tissue, synthetic bone substitute, as well as a medication, or combinations thereof.

In the illustrated embodiment, the group 18 comprises material injection instruments 104 and 106 and a material tamping instrument 108, which deliver material at a low delivery pressure, i.e., a pressure no greater than about 360 psi.

A. Low Pressure Material Injection Instruments

In the illustrated embodiment, the material is injected by use of a conventional syringe 104, to which a specially designed injection nozzle 106 is coupled. A manual actuated syringe with a push plunger can be used. Alternatively, a LeVeen Inflation Syringe with threaded plunger can be used, which can be actuated manually or by use of a mechanical actuator.

In the illustrated embodiment, the syringe 104 is made from a clear plastic material. The syringe 104 includes a chamber 110, which receives the material to be injected. The material is expressed from the chamber 100 by a manually advanced syringe piston 112 (see also FIG. 25).

Figure 25:
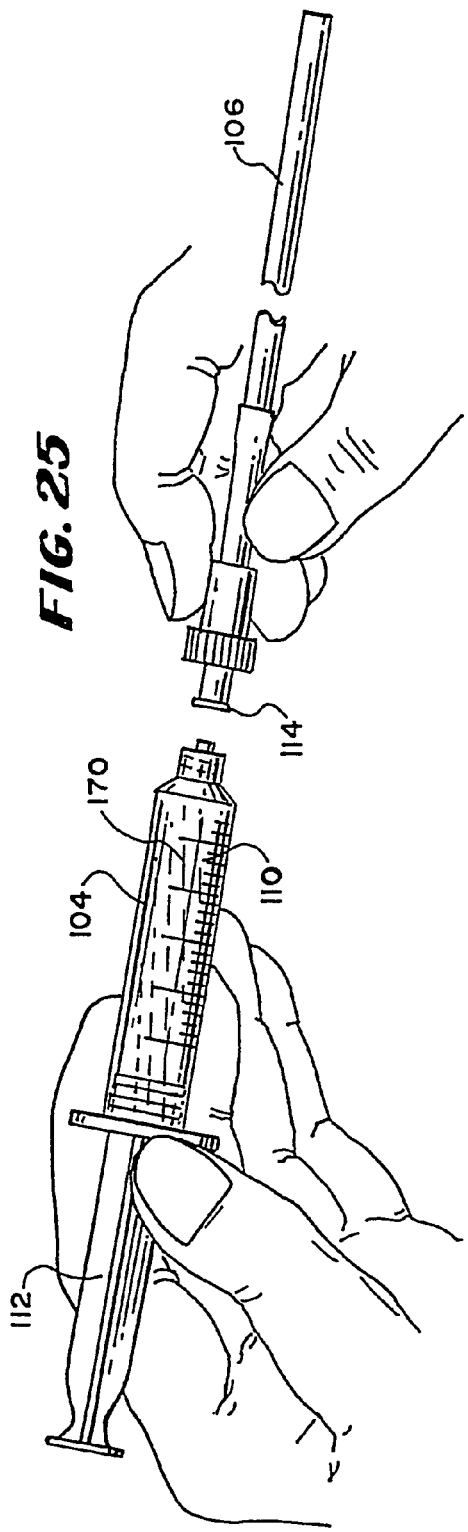
FIG. 25 is a perspective view of the syringe shown in FIG. 24 being joined to a nozzle, which also forms a part of the material introducing instrument group shown in FIG. 5.

The injection nozzle 106 connects by a threaded connector 114 to the end of the syringe 104 (see also FIG. 25). In the illustrated embodiment, the nozzle 106 is made from a generally flexible, inert plastic material, such as such as polyethylene or another suitable polymer. Alternatively, the nozzle 106 can be made from a generally rigid plastic or metal material.

Figure 26:
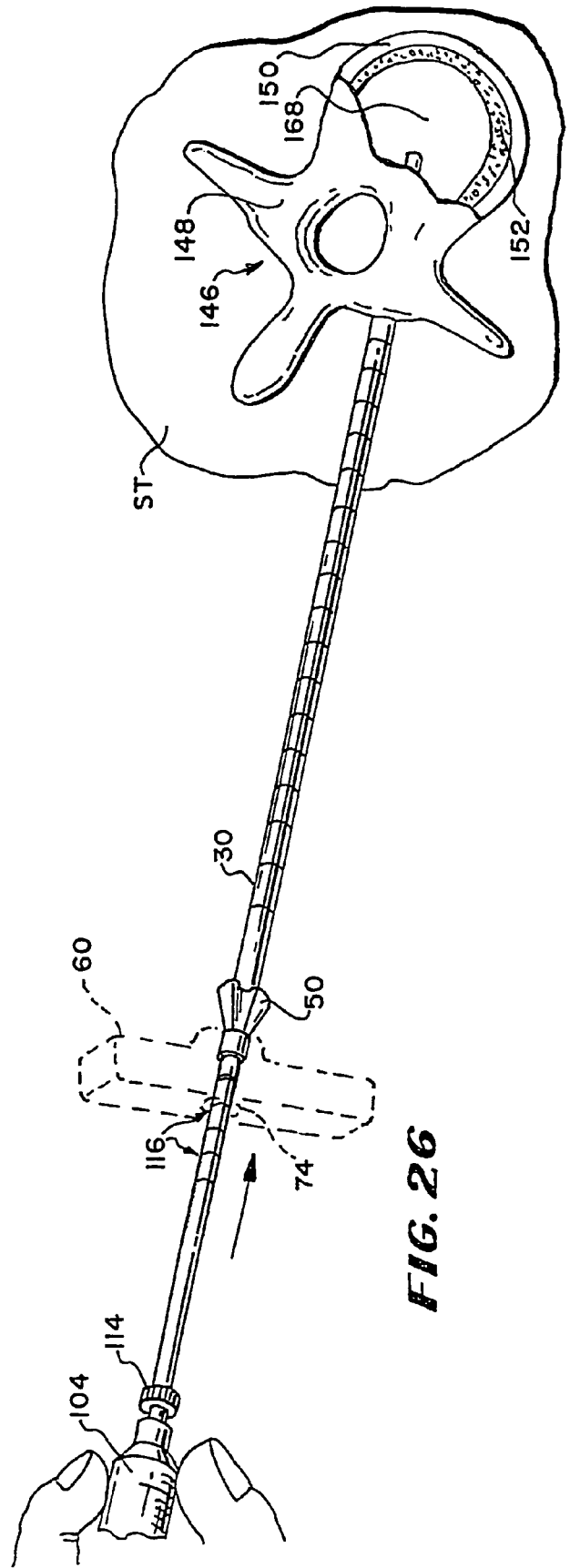
FIG. 26 is a perspective view showing the syringe and attached nozzle shown in FIG. 25 being deployed through the cannula instrument in preparation of introducing material into the cavity.

The injection nozzle 106 is sized to be advanced through the cannula instrument 30 (see FIG. 26). The nozzle 106 includes measured markings 116 along its length. The markings 116 can be placed, for example, at one centimeter intervals, to correspond with the markings 118 on the cannula instrument 30, so that the relative position of the nozzle 106 within the cannula instrument 30 can be gauged. The markings 118 can, e.g., include a set point 176. Alignment of the set point 176 at the proximal end 34 of the cannula instrument 30, indicates that the distal end of the nozzle 106 is located in an aligned relationship with the distal end 36 of the cannula instrument 30. In this arrangement, the markings 118 are consecutively numbered with positive numbers proximally of the set point 176 and with negative numbers distally of the set point 176. The physician is thereby able to tell at a glance the location of the distal end of the nozzle 106, in terms of how far beyond or short of the distal end 36 of the cannula instrument 30 it is.

In use, the distal end of the nozzle 106 is located beyond the distal end 36 of the cannula instrument 30 within the cavity formed in the targeted tissue region. As FIG. 5 shows, the distal end of the nozzle 106, when made from a plastic material, can carry at least one radiopaque marker 208, to enable remote visualization of the nozzle position within the body. The syringe 104 ejects a predetermined volume of material into the nozzle 106 in a low pressure stream into the cavity. As the material fills the cavity, the nozzle (still ejecting material) is retracted from the cavity and into the cannula instrument 30 itself. Further details of this function and result will be provided later.

B. The Material Tamping Instrument

The group 18 also includes a material tamping instrument 108. The tamping instrument 108 is made from generally rigid, inert plastic or metal material. The tamping instrument 108 is also sized to be advanced into the cannula instrument 30 (see FIG. 30). The free end 124 of the tamping instrument 108 is ribbed or contoured to facilitate gripping the instrument 108 during use.

The tamping instrument 108 includes measured markings 122 along its length. The markings 116 can be placed, for example, at one centimeter intervals, to correspond with the markings 118 on the cannula instrument 30, so that the relative position of the tamping instrument 108 within the cannula instrument 30 can be gauged. Like the nozzle 106, the markings 122 on the tamping instrument 108 includes a set point 178, which indicates when the distal end of the tamping instrument 108 aligns with the distal end 36 of the cannula instrument 30. Also like the nozzle 106, the markings 122 on the tamping instrument 108 are consecutively numbered with positive numbers proximally of the set point 178 and with negative numbers distally of the set point 178. The physician is thereby able to tell at a glance the location of the end of the tamping instrument 108, in terms of how far beyond or short of the distal end 36 of the cannula instrument 30 it is. As FIG. 5 also shows, the end of the tamping instrument 108, when made from a plastic material, can carry at least one radiopaque marker 210, so that its position can be visualized from outside the body.

After withdrawal of the nozzle 106 from the cannula instrument 30, residual material is left in the cannula instrument 30. The purpose of the tamping instrument 108 is to displace the residual material out the distal end 36 of the cannula instrument 30 and into the cavity, to thereby fill the cavity without exerting undue pressure within the bone. The tamping instrument 108 thereby serves to clear residual material from the cannula instrument 30, to assure that the desired volume of material is delivered into the cavity. The removal of residual material from the cannula instrument 30 by the tamping instrument 108 also prevents seepage of material into surrounding tissue regions upon removal of the cannula instrument 30. The tamping instrument 108 also compacts the material uniformly within the cavity, again without undue pressure. Further details of these functions and results will be discussed later.

IV. The Kit

As FIGS. 1 and 2 show, in the illustrated embodiment, the kit 12 includes an interior tray 126 made, e.g., from die cut cardboard, plastic sheet, or thermo-formed plastic material. The tray 126 includes spaced apart tabs 128, which hold the various instruments in a secure position during sterilization and storage prior to use.

When packaged as a sterile assembly, the kit 12 includes an inner wrap 130, which is peripherally sealed by heat or the like, to enclose the tray 126 from contact with the outside environment. One end of the inner wrap includes a conventional peal-away seal 132, to provide quick access to the tray 126 at the instant of use, which preferably occurs in a sterile environment, such as within an operating room.

When packaged as a sterile assembly, the kit 12 also includes an outer wrap 134, which is also peripherally sealed by heat or the like, to enclosed the inner wrap 130. One end of the outer wrap includes a conventional peal-away seal 136, to provide access to the inner wrap 130 and its contents. The outer wrap 134 can be removed from the inner wrap in anticipation of imminent use, without compromising sterility of the contents of the kit 12.

As FIG. 2 shows, each inner and outer wrap 130 and 134 includes a peripherally sealed top sheet 138 and bottom sheet 140. In the illustrated embodiment, the top sheet 138 is made of transparent plastic film, like polyethylene or MYLAR7 material, to allow visual identification of the contents of the kit 12. The bottom sheet 140 is made from a material that is permeable to ETO sterilization gas, e.g., TYVEK7 plastic material (available from DuPont).

In the illustrated embodiment, the tray 126 presents the instruments groups 14, 16, and 18 in an ordered, organized layout, which is arranged to aid the physician in carrying out the intended procedure. For example, the layout of the tray 126 can present the instruments groups 14, 16, and 18 in top-to-bottom order, according to sequence of intended use. For example, in a typical bone access procedure (as will be demonstrated in greater detail later), the stylet 22 and stylus 24 of the spinal needle assembly 20 are deployed first, followed by the guide pin instrument 26, followed by the obturator instrument 28, then the cannula instrument 30, then the drill bit instrument 32, then the cavity forming instrument 76, then the syringe 104 and nozzle 106 instruments, and lastly the tamping instrument 108. Accordingly, the tray 126 packages these instruments and components in a top-to-bottom order, with the spinal needle assembly 20 topmost, the guide pin instrument 26 next, the obturator instrument 28 next, and so on, with the tamping instrument 108 lowermost on the tray 126.

In this layout, the handle 60 is packaged to the side of the access instrument group 14. The tray 126 can include written labels (not shown) identifying the components contained in the kit 12.

The kit 12 also preferably includes in the tray 126 directions 144 for using the contents of the kit 12 to carry out a desired procedure. An exemplary procedure which the directions 144 can describe will be explained later.

When packaged as a sterile assembly, the directions 144 can also include the statement "For Single Patient Use Only" (or comparable language) to affirmatively caution against reuse of the contents of the kit 12 whose performance characteristics and efficacy degrade after a single use. The spinal needle assembly 20, the cavity forming instrument 76, and the material introducing instruments 104, 106, and 108 should, for these reasons, be used but a single time and then discarded. The directions 144 also preferably affirmatively instruct against resterilization of at least these contents of kit 12, and also instructs the physician to dispose of at least these contents of the kit 12 upon use in accordance with applicable biological waste procedures.

The presence of the instrument groups 14, 16, and 18 packaged in the sterile kit 12 verifies to the physician that the contents are sterile and have not been subjected to prior use. The physician is thereby assured that the instrument groups meet established performance and sterility specifications.

It should be appreciated that the various instruments contained in the kit 12 can be packaged into several, smaller functional kits. For example, a first kit can package the access instrument group 14, a second kit can package the cavity forming instrument group 16, and a third kit can package the material introduction instrument group 18. FIGS. 1 and 2 illustrate one of many different possible embodiments.

V. Illustrative Use of the System

The following describes use of the instrument groups 14, 16, and 18 packaged in the kit 12 in the context of treating bones. This is because the instruments of the groups 14, 16, and 18 can be advantageously used for this purpose. Still, it should be appreciated that one or more of the instrument groups, used alone or in association with other instruments, can perform other diagnostic or therapeutic functions in other interior regions of the body.

In particular, the instrument groups 14, 16, and 18 will described with regard to the treatment of human vertebra. It should be appreciated, however, their use is not limited to human vertebrae. The instrument groups 14, 16, and 18 can be used in association with hand-held instruments in the treatment of diverse human or animal bone types.

A. The Vertebral Body

Figure 6:
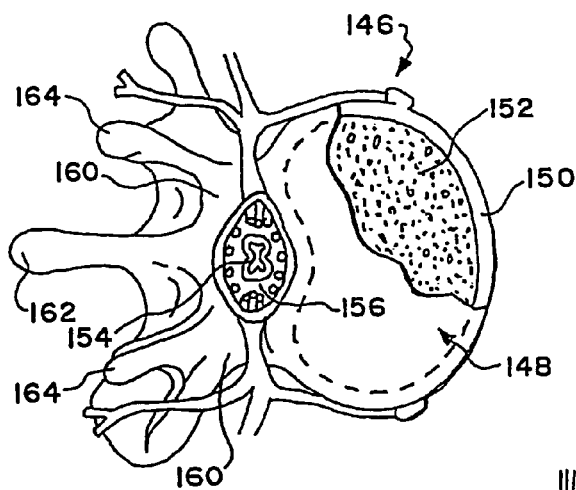
FIGS. 6 and 7 are, respectively, top and side views of a human vertebral body.
Figure 7:
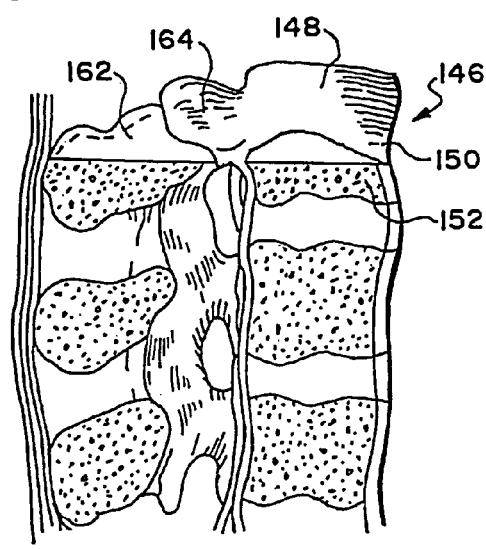

As FIGS. 6 and 7 show, a typical vertebra 146 includes a vertebral body 148, which extends on the anterior (i.e., front or chest) side of the vertebra 146. The vertebral body 148 has the shape of an oval disk. The vertebral body 148 includes an exterior formed from compact cortical bone 150. The cortical bone 150 encloses an interior volume of reticulated cancellous, or spongy, bone 152 (also called medullary bone or trabecular bone).

The spinal cord 154 passes through the spinal canal 156 of the vertebra 146. The vertebral arch 158 surrounds the spinal canal 156. The pedicles 160 of the vertebral arch 158 adjoin the vertebral body 148. The spinous process 162 extends from the posterior of the vertebral arch 158, as do the left and right transverse processes 164.

B. Treatment of a Vertebral Body

During a typical procedure, a patient lies on an operating table. The patient can lie face down on the table, or on either side, or at an oblique angle, depending upon the physician's preference.

Figure 8:
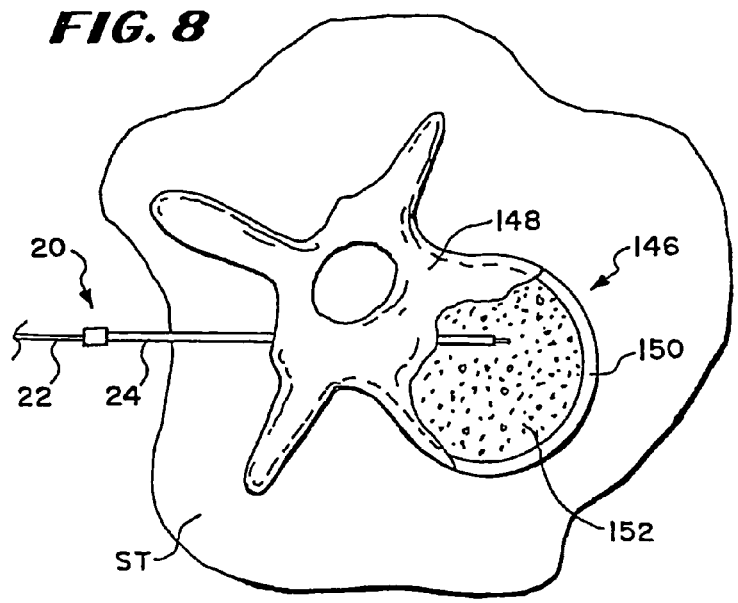
FIG. 8 is a top view of a vertebral body during insertion of a spinal needle instrument to begin a bone access procedure.

The physician or surgical assistant removes the outer and inner wraps 130 and 134 of the kit 12, exposing the tray 126 for use. The physician acquires the spinal needle assembly 20 from the tray 126. As FIG. 8 shows, the physician introduces the spinal needle assembly 20 into soft tissue ST in the patient's back. Under radiologic or CT monitoring, the physician advances the spinal needle assembly 20 through soft tissue down to and into the targeted vertebra 146. The physician will typically administer a local anesthetic, for example, lidocaine, through assembly 20. In some cases, the physician may prefer other forms of anesthesia.

The physician directs the spinal needle assembly 20 to penetrate the cortical bone 150 and the cancellous bone 152 of the targeted vertebral body 148. Preferably the depth of penetration is about 60% to 95% of the vertebral body 148.

FIG. 8 shows gaining access to cancellous bone through the side of the vertebral body 148, which is called posterolateral access. However, access may be indicated through a pedicle 160, which is called transpedicular access. The type of access is based upon the objectives of the treatment or for other reasons, based upon the preference of the physician.

Figure 9:
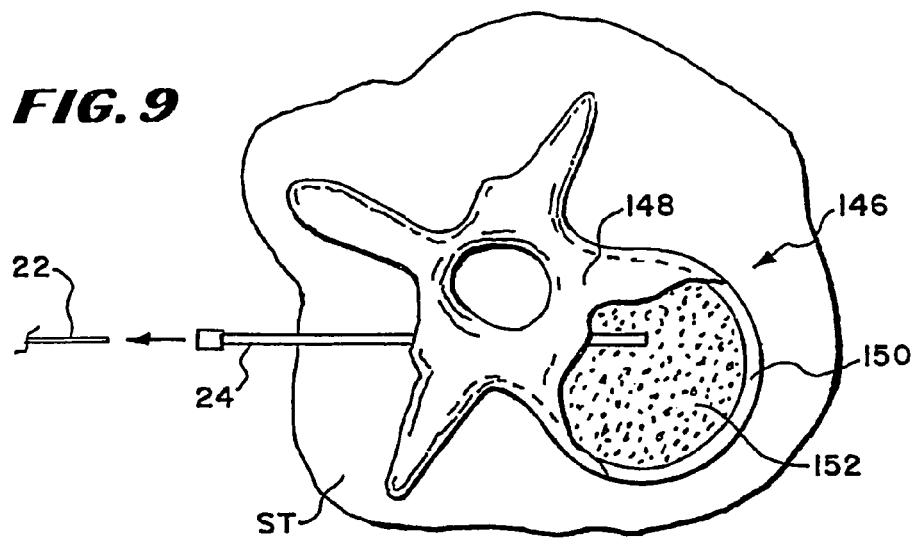
FIGS. 9 to 11 are top views showing subsequent steps, after insertion of the spinal needle instrument shown in FIG. 8, of inserting a guide pin instrument into the vertebral body.
Figure 10:
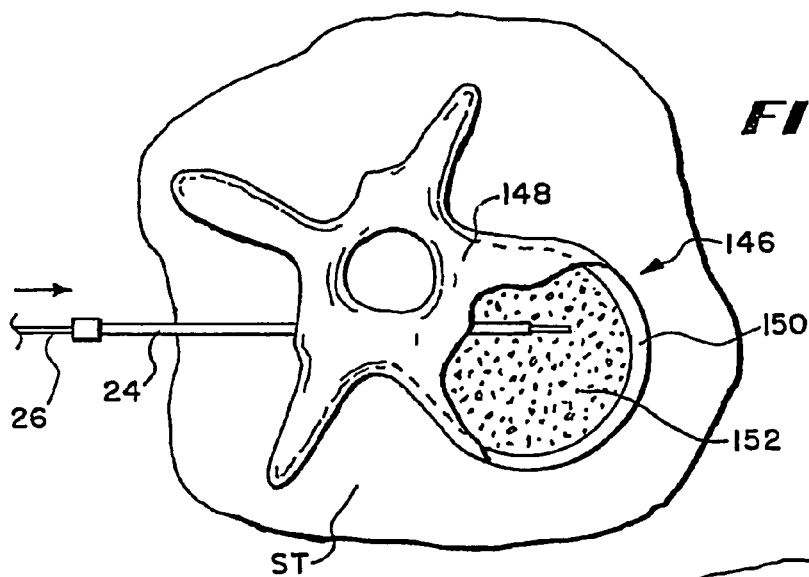
Figure 11:
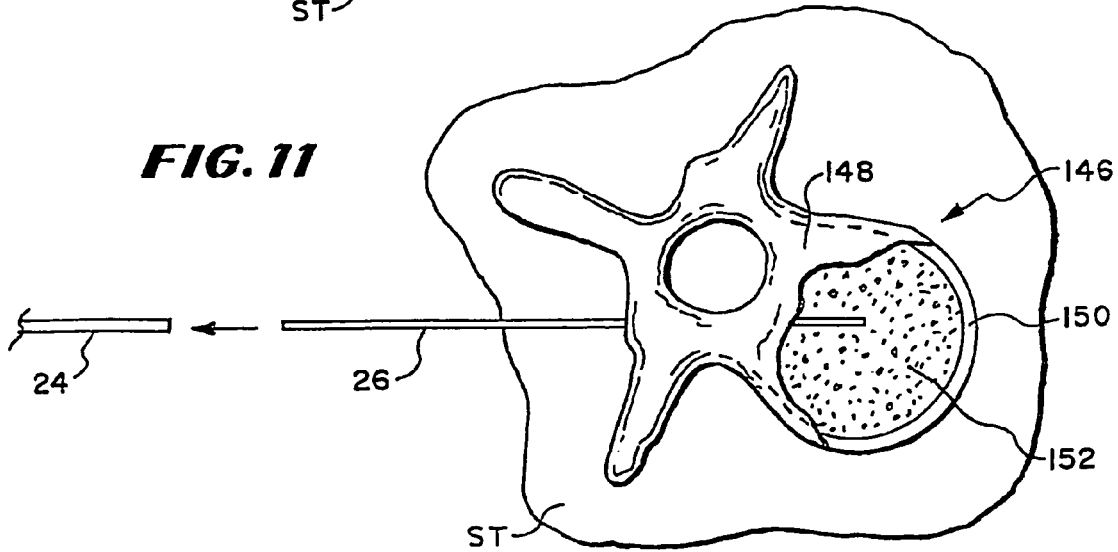

As FIG. 9 shows, after positioning the spinal needle assembly 20 in cancellous bone 152, the physician holds the stylus 24 and withdraws the stylet 22. The physician acquires the guide pin instrument 26 from the tray 126. As FIG. 10 shows, while still holding the stylus 24, the physician slides the guide pin instrument 26 through the stylus 24 and into the cancellous bone 152. The physician now removes the stylus 24 (see FIG. 11), leaving the guide pin instrument 26 deployed within the cancellous bone 152.

The physician next acquires the obturator instrument 28 and the handle 60 from the tray 126. The physician slides the obturator instrument 28 over the guide pin instrument 26, distal end first. The physician slides the guide pin instrument 26 through the first passage 72 and the first socket 64 of the handle 60. As FIG. 12 shows, the physician slides the handle 60 along the guide pin instrument 26 toward the tapered flange 40 of the obturator instrument 28, until achieving a running slip-fit between the first socket 64 and the tapered flange 40, in the manner previously described. The obturator instrument 28 is now ready for use.

As FIG. 12 shows, the physician makes a small incision I in the patient's back. The physician twists the handle 60 while applying longitudinal force to the handle 60. In response, the surface 38 of the obturator instrument 28 rotates and penetrates soft tissue ST through the incision I. The physician may also gently tap the handle 60, or otherwise apply appropriate additional longitudinal force to the handle 60, to advance the obturator instrument 28 through the soft tissue along the guide pin instrument 26 down to the entry site (see FIG. 13). The physician can also tap the handle 60 with an appropriate striking tool to advance the surface 30 of the obturator instrument 28 into the side of the vertebral body 148 to secure its position (as FIG. 13 shows).

The physician next slides the handle 60 along the guide pin instrument 26 away from the obturator instrument 28 to disengage the tapered flange 40 from the first socket 64. The physician then proceeds to slide the handle 60 completely off the guide pin instrument 26.

The physician acquires the cannula instrument 30 from the tray 126. As FIG. 14 shows, the physician slides the cannula instrument 30 over the guide pin instrument 26, distal end first, and, further, over the obturator instrument 28, until contact between the end surface 48 and soft tissue ST. The physician now slides the guide pin instrument 26 and obturator instrument 26 through the second passage 74 and second socket 66 of the handle 60. The physician slides the handle 60 toward the tapered fitting 50 of the cannula instrument 30 until a running slip-fit occurs between the second socket 66 and the tapered fitting 50, as previously described. The cannula instrument 30 is now ready for use.

As FIG. 14 shows, the physician applies appropriate twisting and longitudinal forces to the handle 60, to rotate and advance the cannula instrument 30 through soft tissue ST along the obturator instrument 28. As FIG. 15 shows, when the end surface 48 of the cannula instrument 30 contacts cortical bone, the physician can appropriately tap the handle 60 with a striking tool to advance the end surface into the side of the vertebral body 148 to secure its position.

As FIG. 16 shows, the physician now withdraws the obturator instrument 28, sliding it off the guide pin instrument 26. This leaves the guide pin instrument 26 and the cannula instrument 30 in place, as FIG. 17 shows. The physician next slides the handle 60 along the guide pin instrument 26 away from the cannula instrument 30 to disengage the tapered fitting 50 from the second socket 66. The physician then slides the handle 60 completely off the guide pin instrument 26.

The physician now acquires the drill bit instrument 32 from the tray 126. As FIG. 18 shows, the physician slides the drill bit instrument 32 over the guide pin instrument 26, distal end first, through the cannula instrument 30 until contact between the machined surface 54 and bone tissue occurs. As FIG. 18 also shows, the physician next leads the guide pin instrument 26 through the first passage 72 and first socket 64 of the handle 60. The physician slides the handle 60 along the guide pin instrument 26 toward the tapered flange 56 of the drill bit instrument 32, until a running slip-fit occurs between the first socket 64 and the tapered flange 56, as previously described. The drill bit instrument 32 is now ready for use.

As shown by FIG. 18, guided by X-ray (or another external visualizing system), the physician applies appropriate twisting and longitudinal forces to the handle 60, to rotate and advance the cutting edge 54 of the drill bit instrument 32 to open a passage 166 (see FIG. 19) through the bone tissue and completely into the cancellous bone 152. The drilled passage 166 preferable extends no more than 95% across the vertebral body 148.

The physician now slides the handle 60 along the guide pin instrument 26 away from the drill bit instrument 32 to disengage the tapered flange 56 from the first socket 64. The physician, further, slides the handle 60 completely off the guide pin instrument 26.

The physician can now remove the drill bit instrument 32 and the guide pin instrument 26, leaving only the cannula instrument 30 in place. The passage 166 made by the drill bit instrument 32 remains. Subcutaneous access to the cancellous bone 152 has been accomplished.

The physician can now acquire the cavity forming instrument from the tray 126. As FIG. 20 shows, the physician can advance the expandable structure 86 through the cannula instrument 30 and passage 166 into the interior volume of the vertebral body 148, as FIG. 21 also shows. The structure 86 is in its normally collapsed and not expanded condition during deployment. The stylet 96 or 102 is inserted in the lumen 94 of the catheter tube 78 to provide added stiffness to the structure 86 while being passed through the cannula instrument 30.

As shown in phantom lines in FIG. 20, the physician can, if desired, reconnect the handle 60 to the cannula instrument 30, to help stabilize the cannula instrument 30 while deploying the structure 86. The second passage 74 of the handle accommodates the catheter tube 78 and the structure 86, when collapsed.

As FIG. 21 shows, the structure 86 is oriented in the desired way in the passage 166. As before explained, the bent stylet 102 can aid in this task. Before, during, or after the orientation process, the stylet 96 or 102 can be withdrawn (as FIG. 21 shows), to open the lumen 94 for use to pass a rinsing liquid or negative aspiration pressure.

Sterile liquid is conveyed under pressure from the source 92 through the lumen 88 into the structure 86. As FIG. 22 shows, the structure 86 expands inside bone. Expansion of the structure 86 compresses cancellous bone 152 in the vertebral body 148.

The compression forms an interior cavity 168 in the cancellous bone 152. As FIG. 23 shows, subsequent collapse and removal of the structure 86 leaves the cavity 168 in a condition to receive a filling material.

The compaction of cancellous bone 152 can also exert interior force upon cortical bone, making it possible to elevate or push broken and compressed bone back to or near its original prefracture, or other desired, condition.

Upon formation of the cavity 168, the physician acquires the syringe 104 and injection nozzle 106 from the kit 12. As FIG. 24 shows, the physician fills the syringe chamber 110 with the desired volume of filling material 170. As FIG. 25 shows, the physician attaches the nozzle 106 to the filled syringe 104. As FIG. 26 shows, the physician inserts the nozzle 106 a selected distance beyond the distal end 36 of the cannula instrument 30 and into the cavity, guided by the markings 116.

As shown in phantom lines in FIG. 26, the handle 60 can remain attached to the cannula instrument 30 to provide stability, as the second passage 74 of the handle accommodates the nozzle 106.

As FIG. 27 shows, the physician manually advances the piston 112 to cause the material 170 to flow through and out of the nozzle 106 and into the cavity. As material 170 fills the cavity, the physician withdraws the nozzle from the cavity and into the cannula instrument 30. The cannula instrument 30 channels the material 170 flow toward the cavity 168. As FIG. 28 shows, the cement material 170 flows in a stream into the cavity 168.

If the selected material 170 is bone cement, the cement material 170 is placed into the syringe chamber 110 shortly after it is mixed from two materials (e.g., in an external mixing device), while it is in a low viscosity, relatively free flowing liquid state, like a thin pancake batter. In time (e.g., about two minutes after mixing), the consistency of the cement material 170 will change to a substantially putty-like character.

The physician operates the syringe 104 to expel the cement material 170 from the chamber, through the nozzle 106, first into the cavity and then into the cannula instrument 30. Typically, at the end of the syringe injection process, material 170 should extend from the cavity and occupy about 40% to 50% of the cannula instrument 30.

When a desired volume of cement is expelled from the syringe 104, the physician withdraws the nozzle 106 from the cannula instrument 30, as FIG. 29 shows. The physician may first rotate the syringe 104 and nozzle 106, to break loose the material 170 in the nozzle 106 from the ejected bolus of material 170 occupying the cannula instrument 30.

The physician acquires the tamping instrument 108 from the kit 12. As FIG. 30 shows, the physician advances the tamping instrument 108 through the cannula instrument 30. As phantom lines in FIG. 30 show, the handle 60 can remain attached to the cannula instrument 30 to provide stability, as the second passage 74 of the handle accommodates the tamping instrument 108.

The distal end of the tamping instrument 108 contacts the residual volume of cement material 170 in the cannula instrument 30. As FIGS. 30 and 31 show, advancement of the tamping instrument 108 displaces progressively more of the residual material 170 from the cannula instrument 30, forcing it into the cavity 168. The flow of material 170 into the cavity 168, propelled by the advancement of the tamping instrument 108 in the cannula instrument 30, serves to uniformly distribute and compact the material 170 inside the cavity 168, without the application of undue pressure.

The use of the syringe 104, nozzle 106, and the tamping instrument 108 allows the physician to exert precise control when filling the cavity with material 170. The physician can immediately adjust the volume and rate of delivery according to the particular local physiological conditions encountered. The application of low pressure (i.e., no greater than 360 psi), which is uniformly applied by the syringe 104 and the tamping instrument 108, allows the physician to respond to fill volume and flow resistance conditions in a virtually instantaneous fashion. The chance of overfilling and leakage of material 170 outside the cavity is significantly reduced.

When the physician is satisfied that the material 170 has been amply distributed inside the cavity 168, the physician withdraws the tamping instrument 108 from the cannula instrument 30. The physician preferably first twists the tamping instrument 108 to cleanly break contact with the material 170. The handle 60 can now be removed and the cannula instrument 30 withdrawn, as FIG. 32 shows. The incision site is sutured closed. The bone treatment procedure is concluded.

Eventually the material 170, if cement, will harden a rigid state within the cavity 168. The capability of the vertebral body 148 to withstand loads is thereby improved.

The selected material 170 can be an autograft or allograft bone graft tissue collected in conventional ways. For example, the graft material can be in paste form, as described by Dick, A Use of the Acetabular Reamer to Harvest Autogenic Bone Graft Material: A Simple Method for Producing Bone Paste,@ Archives of Orthopaedic and Traumatic Surgery (1986), 105: 235-238, or in pellet form, as described by Bhan et al, A Percutaneous Bone Grafting for Nonunion and Delayed Union of Fractures of the Tibial Shaft, International Orthopaedics (SICOT) (1993) 17: 310-312, both of which are incorporated herein by reference. Alternatively, the bone graft tissue can be obtained using a Bone Graft Harvester, which is commercially available from SpineTech. Using a funnel, the paste or pellet graft tissue material is loaded into the cannula instrument 30. The tamping instrument 108 is then advanced into the cannula instrument 30 in the manner previously described, to displace the paste or pellet graft tissue material out of the cannula instrument 30 and into the cavity.

The selected material 170 can also comprise a granular bone material harvested from coral, e.g., ProOsteonJ calcium carbonate granules, available from Interpore. The granules are loaded into the cannula instrument 30 using a funnel and advanced into the cavity using the tamping instrument 108.

The selected material 170 can also comprise demineralized bone matrix suspended in glycerol (e.g., GraftonJ allograft material available from Osteotech), or SRSJ calcium phosphate cement available from Novian. These viscous materials, like the bone cement previously described, can be loaded into the syringe 104 and injected into the cavity using the nozzle 106, which is inserted through the cannula instrument 30 into the cavity. The tamping instrument 108 is used to displace residual material from the cannula instrument 30 into the cavity, as before described.

The selected material 170 can also be in sheet form, e.g. CollagraftJ material made from calcium carbonate powder and collagen from bovine bone. The sheet can be rolled into a tube and loaded by hand into the cannula instrument 30. The tamping instrument 108 is then advanced through the cannula instrument, to push and compact the material in the cavity.

VI. Alternative Embodiments

The use of low pressure delivery of material 170 frees the system 10 from the need to accommodate relatively large diameter, high pressure delivery devices. The interior diameter of the cannula instrument 30 can be downsized accordingly, thereby minimizing the dimensions of the subcutaneous pathway to gain access to the targeted bone region.

Typically, when low pressure material injection instruments are used, the largest tool that the reduced-diameter cannula instrument must accommodate is the expandable cavity-forming structure 82. The structure 82 presents a minimal profile during deployment, as it can be collapsed and, if desired, a lubricous coating may also be applied to the exterior of the structure 82 to facilitate its passage through the reduced-diameter cannula instrument.

A. Low Pressure Material Injection Instruments

Figure 33:
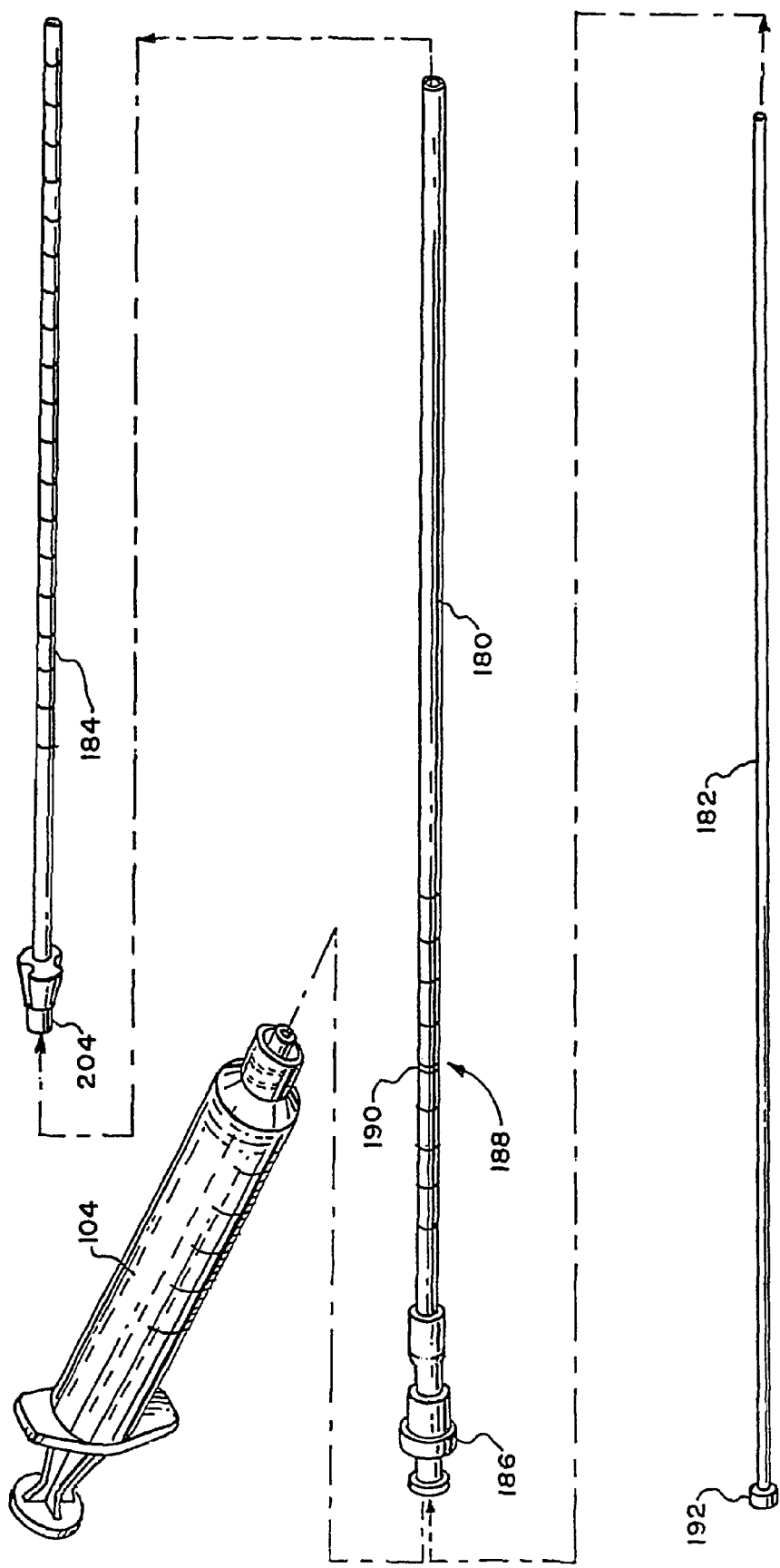
FIG. 33 is a perspective view of a reduced diameter cannula instrument and associated reduced diameter material introducing instruments, which embody features of the invention.

FIG. 33 exemplifies low pressure material injection instruments 180 and 182 that function in association with a cannula instrument 184 having a reduced interior diameter, e.g. only about 3.4 mm or less.

One instrument 180 comprises a reduced-diameter nozzle. As FIG. 33 shows, the nozzle 180 is sized to pass through the reduced-diameter cannula instrument 184, to thereby pass into bone in the manner previously shown in FIG. 26. The reduced-diameter nozzle 180 connects by a threaded connector 186 to the syringe 104. For material strength, despite its reduced dimension, the nozzle 180 is preferably formed from a rigid metal material, e.g., stainless steel.

As FIG. 33 shows, the reduced-diameter nozzle 180 also includes measured markings 188 along its length, as previously described. The markings 188 include a set point 190, as previously described, which aligns with the proximal end of the cannula instrument 184 when the distal ends of the cannula instrument 184 and the nozzle 180 align.

The other reduced diameter instrument 182 comprises a stylet, which is sized to pass through the interior bore of the nozzle 180. The stylet 182 includes a handle 192, which rests on the proximal connector 186 of the nozzle 180 when the stylet 182 is fully inserted into the nozzle 180. When the handle 192 is rested, the distal ends of the stylet 182 and nozzle 180 align. The presence of the stylet 182 inside the nozzle 180 closes the interior nozzle bore.

In use, the nozzle 180 is coupled to the syringe 104 and inserted through the cannula instrument 184 into the materialreceiving cavity 168 formed in cancellous bone, in the same manner shown in FIG. 26. Material in the syringe 104 is injected at low pressure through the nozzle 180 into the cavity 168. As before explained, as the cavity 168 progressively fills with material, the nozzle 180 is withdrawn back into the cannula instrument 184. Typically, when the injection of material is completed, material extends from the cavity 168 and occupies about 40% to 50% of the cannula instrument 184.

At this point, the nozzle 180 can be fully withdrawn from the cannula instrument 184 and unthreaded from the syringe 104. The stylet 182 can be advanced into the nozzle 180, to bring the handle 192 at rest against the connector 186, thereby clearing residual material from the nozzle 180. The nozzle 180 and stylet can then be inserted as a nested unit into the cannula instrument 184. Nested together, the nozzle 180 and stylet 182 form a tamping instrument. Upon advancement through the cannula instrument 184, the nested nozzle 180 and stylet 182 displace residual material from the cannula instrument 184 into the cavity 168, in generally the same manner as previously shown in FIGS. 30 and 31, thereby uniformly compacting material-within the cavity 168 in a controlled fashion and without undue pressure.

Alternatively, a single-piece tamping instrument, separate from the nozzle 180, can be provided, downsized to fit through the reduced-diameter cannula instrument 184. In this embodiment, the stylet 182 is not necessary, unless it is desired to reclaim material from the nozzle.

B. Cavity Forming Instrument

Figure 34:
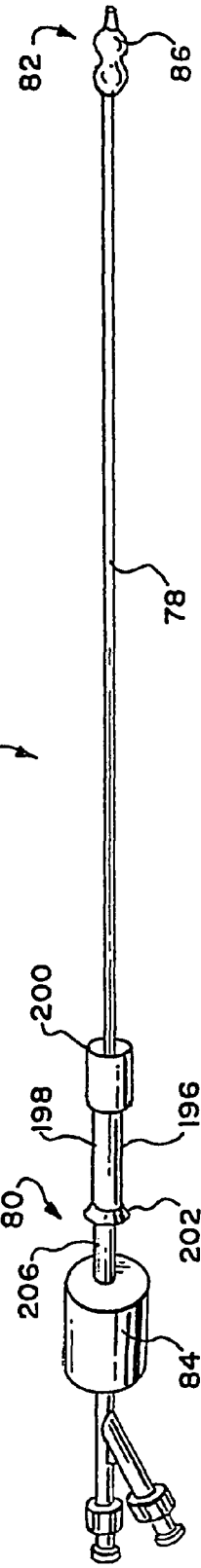
FIG. 34 is a perspective view of a cavity forming instrument having an expandable cavity forming structure, which, in use, is deployed using the reduced diameter cannula instrument shown in FIG. 33, the cavity forming instrument having a sliding introducer sleeve shown in its rearward position.

FIG. 34 shows a cavity forming instrument 194 intended to be deployed through the reduced-diameter cannula instrument 184, shown in FIG. 33. In many respects, the instrument 194 is like the instrument 76, previously described and shown in FIG. 4A, and common reference numerals will be assigned to common structural elements. The instrument 184 includes a flexible catheter tube 78 having a proximal end 80 and a distal end 82. The proximal end 80 carries a handle grip 84, and the distal end 82 carries an expandable structure 86, which, when deployed in bone, compacts cancellous bone and forms the cavity 168.

Unlike the previously-described instrument 76, the instrument 194 carries an introducer sleeve 196. The introducer sleeve 196 slides along the catheter tube 78 between the handle grip 84 and the expandable structure 86. The introducer sleeve 196 includes a tubular main body 198 with a forward collar 200 and a rear collar 202.

Figure 35:
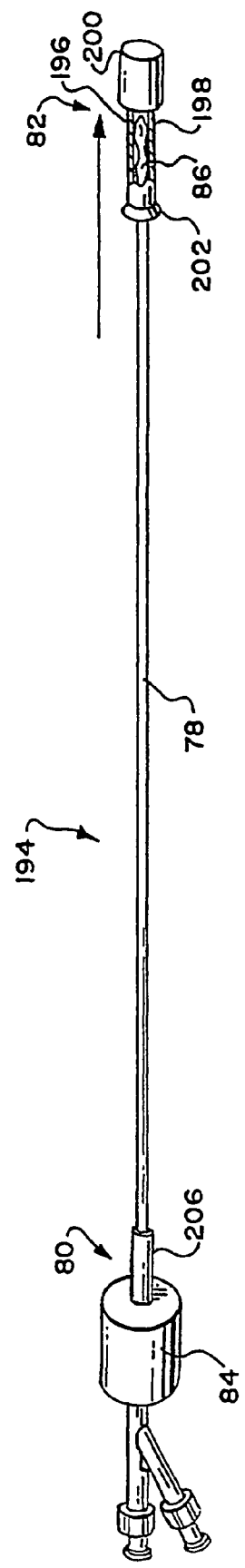
FIG. 35 is a perspective view of the cavity forming instrument shown in FIG. 34, with the introducer sleeve moved forward to overlie and compress the expandable cavity forming structure.

The introducer sleeve 196 normally occupies an advanced position on the instrument 194, as shown in FIG. 35. In this position, the main body 198 overlies and surrounds the expandable structure 86. The main body 198 is sized to compress the structure 86 to an outside diameter that is slightly less than the interior diameter of the reduced-diameter cannula instrument 184.

As FIG. 35 shows, when the introducer sleeve 196 occupies the advanced position, the forward collar 200 extends beyond the distal end of the compressed expandable structure 82. As FIG. 36 shows, in this position, the forward collar 200 presents itself for engagement with the proximal end 204 of the cannula instrument 184. The forward collar 200 is sized to have an interior diameter that makes friction-fit engagement about the proximal end 204 of the cannula instrument 184.

As FIG. 36 shows, when it is time to deploy the expandable structure 86 through the cannula instrument 184, the physician engages the forward collar 200 of the introducer sleeve 196 in a friction fit about the proximal end 204 of the cannula instrument 184. As FIG. 37 shows, advancing the catheter tube 78 moves the compressed structure 86 through the main body 198 of the sleeve 196 and into the bore of the cannula instrument 184. The engagement of the forward collar 200 about the proximal cannula end 204 aligns the axis of the structure 86 with the axis of the cannula instrument 184, while compressing the structure 86 to a diameter smaller than the interior of the cannula instrument 184. Upon advancement of the catheter tube 78, the introducer sleeve 196 guides the structure 86 into the cannula instrument 194 without tearing or other damage.

Once the expandable structure 86 is advanced through the cannula instrument 184 and into bone, the physician can slide the introducer sleeve 196 rearward away from the proximal cannula end 204, to break the friction fit between the end 204 and the forward sleeve. As FIG. 34 shows, the rear collar 202 of the sleeve 196 is sized to make a snap fit engagement about a stem 206, which surrounds the catheter tube 78 near the handle 84. The snap fit engagement stabilizes the position of the sleeve 196 during subsequent use and manipulation of the cavity-forming instrument 194.

The features of the invention are set forth in the following claims.

We claim:

1. A method comprising
deploying a cannula through soft tissue to establish a subcutaneous path into bone,
deploying a cavity forming instrument through the cannula to form a cavity in cancellous bone, and
introducing a material into the cavity through the cannula including injecting first and second portions of the material respectively into the cavity and into the interior of the cannula and then advancing a tamping instrument through the cannula to urge the second portion of the material from the interior of the cannula into the cavity.

2. A method according to claim 1 wherein introducing includes delivering material at a pressure no greater than about 360 psi.

3. A method according to claim 2 wherein introducing includes using a manual syringe.

4. A method according to claim 1 wherein the material comprises bone cement.

5. A method according to claim 1 wherein the material comprises autograft tissue.

6. A method according to claim 1 wherein the material comprises allograft tissue.

7. A method according to claim 1 wherein the material comprises synthetic bone substitute.

8. A method according to claim 1 wherein the material comprises medication.

9. A method according to claim 1 wherein the material comprises a material that sets to a hardened condition.

10. A method according to claim 1 wherein the cavity forming instrument includes an expandable body, and
wherein deploying the cavity forming instrument includes expanding the expandable body to form the cavity.

11. A method according to claim 10 wherein expanding the expandable body compresses cancellous bone.

12. A method according to claim 10 wherein expanding the expandable body moves fractured cortical bone.

13. A method according to claim 10 wherein the expandable body expands by inflation.

14. A method according to claim 10 wherein the expandable body includes a balloon.

* * * * *